United States Patent
Nakano et al.

(10) Patent No.: US 8,535,943 B2
(45) Date of Patent: Sep. 17, 2013

(54) BLOOD PLATELET INDUCTION METHOD

(75) Inventors: Yasuhiro Nakano, Tokyo (JP); Nobuyuki Takakura, Suita (JP)

(73) Assignee: Osaka University, Suita-Shi, Osaka (JP)

(*) Notice: Subject to any disclaimer, the term of this patent is extended or adjusted under 35 U.S.C. 154(b) by 199 days.

(21) Appl. No.: 12/992,429

(22) PCT Filed: May 15, 2009

(86) PCT No.: PCT/JP2009/002131
§ 371 (c)(1),
(2), (4) Date: Nov. 22, 2010

(87) PCT Pub. No.: WO2009/139177
PCT Pub. Date: Nov. 19, 2009

(65) Prior Publication Data
US 2011/0065190 A1    Mar. 17, 2011

(30) Foreign Application Priority Data

May 15, 2008 (JP) .................. 2008-128389
May 14, 2009 (JP) .................. 2009-117105

(51) Int. Cl.
*C12N 5/00* (2006.01)
*C12M 1/12* (2006.01)

(52) U.S. Cl.
USPC ............. 435/377; 435/297.1; 435/325

(58) Field of Classification Search
None
See application file for complete search history.

(56) References Cited

U.S. PATENT DOCUMENTS

2007/0029256 A1    2/2007  Nakano et al.
2007/0077654 A1*   4/2007  Thomson et al. ............. 435/372

FOREIGN PATENT DOCUMENTS

WO    WO 2005/014149 A1    2/2005
WO    WO 2005/100549 A1   10/2005

OTHER PUBLICATIONS

Hasegawa et al., "The history and status of platelet substitute", Artificial Blood, vol. 11, No. 4 (2003) pp. 193-199.
Hoffmeister et al., "Glycosylation Restores Survival of Chilled Blood Platelets", Science, vol. 301 (2003) p. 1531-1534.
Imahori et al., Seikagaku Jiten (3rd edition), 2nd print, Nov. 20, 1998, p. 373.
Imahori et al., Seikagaku Jiten (3rd edition), 2nd print, Nov. 20, 1998, pp. 461-462.
International Preliminary Report on Patentability issued in International Application No. PCT/JP2009/002131 on Jan. 11, 2011.
International Search Report issued in International Application No. PCT/JP2009/002131 on Jun. 9, 2009.
Jiang et al., "Fibronectin- and protein kinase C-mediated activation of ERK/MAPK are essential for proplateletlike formation", Blood, vol. 99 (2002) pp. 3579-3584.

(Continued)

*Primary Examiner* — Blaine Lankford, Jr.
*Assistant Examiner* — Lauren K Van Buren
(74) *Attorney, Agent, or Firm* — Birch, Stewart, Kolasch & Birch, LLP

(57) ABSTRACT

A novel induction method that effectively produces platelets from platelet precursor cells (e.g., hemopoietic stem/precursor cells) is disclosed. The method includes culturing platelet precursor cells in a culture solution in which a composite membrane is immersed so that the platelet precursor cells differentiate into platelets, the composite membrane including a porous support membrane and a porous thin membrane, the porous thin membrane being stacked on at least one side of the porous support membrane.

11 Claims, 13 Drawing Sheets

(56) References Cited

OTHER PUBLICATIONS

Johnson et al., "Alternation of the Postinjury Hyperinflammatory Response by Means of Resuscitation with a Red Cell Substitute", J. of Trauma Injury, Infection, and Critical Care, vol. 54, No. 1 (2003) pp. 133-140.

Nagata et al., "Proplatelet formation of megakaryocytes is triggered by autocrine-synthesized estradiol", Genes & Development, vol. 17 (2003) pp. 2864-2869.

Okamura et al., "Development of fibrinogen • chain dodecapeptide-conjugated particles", Artificial Blood, vol. 11, No. 4 (2003) pp. 205-210.

Ratajczak et al., "In Vitro and In Vivo Evidence that Ex Vivo Cytokine Priming of Donor Marrow Cells May Ameliorate Posttransplant Thrombocytopenia", Blood, vol. 91 (1998) pp. 353-359.

Teramachi et al., "Effects of Glyocosaminoglycans on the in vitro Colony Formation of CD34+ Megakaryocytic Progenitor Cells in Human Placental/Umbilical Cord Blood", Yakugaku Zasshi, vol. 121, No. 9 (2001) pp. 691-699.

Tsutsui et al., "Duration of Efficacy of NRC (Neo Red Cell) administered in divided doses", Artificial Blood, vol. 11, No. 4 (2003) pp. 200-204.

\* cited by examiner

A

| | Culture condition | Total number of collected cells | Number of megakaryocytes |
|---|---|---|---|
| Comp. example 1 | Liquid culture | $1.33 \times 10^5$ | 310 |
| Comp. example 2 | Culture insert | $1.30 \times 10^5$ | 355 |
| Example 2 | Nonwoven fiber | $6.25 \times 10^5$ | 5000 |
| Example 1 | Composite membrane | $5.40 \times 10^5$ | 4200 | a  Comp. example 1   Liquid culture
b  Comp. example 2   Culture insert
c  Example 2         Nonwoven fiber
d  Example 1         Composite membrane

BLOOD PLATELET INDUCTION METHOD

TECHNICAL FIELD

The present invention relates to platelet production technology that efficiently causes platelet precursor cells to differentiate into platelets and/or megakaryocytes using a specific composite membrane in which a porous thin membrane and a porous support membrane are stacked.

BACKGROUND ART

Platelets are one kind of blood cells having a diameter of 2 to 4 μm, and play a key role in hemostasis and thrombosis in a living body. It is known that platelets are produced as a result of differentiation of undifferentiated hematopoietic cells in the bone marrow into megakaryocytes through megakaryocyte precursor cells, followed by fragmentation of the cytoplasm of the matured megakaryocytes.

Platelet transfusion has been widely used for cancer chemotherapy and treatment of blood diseases such as thrombocytopenia. The current platelet transfusion that relies upon volunteer donors has problems such as
1) a frequent recipient gradually suffers from a platelet transfusion refractory state due to platelet alloantibodies (derived from HLA or HPA),
2) there is a virus infection risk due to transfusion in the window period, and
3) it takes time to collect platelet components and this places a burden on donors, and in medical front platelet products have been deficient due to a decrease in the number of donors year after year. A short storage life (three days) is also one of the reasons for a deficiency in platelet products. Therefore, a method that stores platelets at a low temperature for a long time by modifying the surface sugar chains of platelets has been proposed (Non-patent Document 1). However, this method has not been put to practical use.

Administration of thrombopoietin (TPO) to a patient has been examined as cytokine therapy for thrombocytopenia due to cancer chemotherapy. However, the expected effect has not been achieved. Contrary, the problem of occurrence of an anti-TPO antibody was revealed, and the development has been stopped. Artificial platelets have been developed (Non-patent Document 2), but have not been put to clinical application yet.

In view of the above situation, transfusion alternative therapy (i.e., in vitro platelet production technology) that produces a large amount of platelets by culturing (inducing differentiation of) undifferentiated hematopoietic cells (mainly hemopoietic stem/precursor cells) in vitro, and returns the produced platelets to the living body has been extensively studied along with development of regenerative medicine technology. If platelets can be mass-produced due to development of in vitro platelet production technology in the future, the current blood donation system will become unnecessary, and a deficiency in platelet products and a virus infection risk will be eliminated.

Hematopoietic stem cells can be mainly collected from the bone marrow, cord blood, and peripheral blood as a cell source. When using such a cell source, platelet-transfusion refractoriness and a virus infection risk can be completely eliminated by inducing platelets using hematopoietic stem cells derived from autologous bone marrow or autologous peripheral blood. When using allogeneic bone marrow or cord blood, since it is possible to use hematopoietic stem cells for which HLA almost completely coincides due to recent well-developed system of the bone marrow bank and the cord blood bank, it may become an ideal treatment method similarly.

As to in vitro platelet production technology using undifferentiated hematopoietic cells, (1) technology of inducing differentiation of undifferentiated hematopoietic cells into megakaryocytes, and (2) technology of inducing differentiation of megakaryocytes into platelets are particularly important. Regarding (1) technology of adding TPO, which is typical megakaryocyte induction factor, to the culture system has been mainly reported as basic technique. For example, a combination of TPO and several types of cytokines (Non-patent Document 3), an improvement in megakaryocyte induction/amplification efficiency by combining of TPO and various glycosaminoglycans (Non-patent Document 4) and the like, have been reported. However, a major breakthrough has not been achieved until now. Almost no reports have been made regarding (2) technology of inducing differentiation of megakaryocytes into platelets. Only some reports have been disclosed concerning the release mechanism of platelets from megakaryocytes in vivo (see Non-patent Documents 5 and 6, for example).

Specifically, in vitro platelet production technology using undifferentiated hematopoietic cells has not been completed until now, and a new technical approach has been strongly desired in this technical field. In particular, development of the technology that effectively induces differentiation into megakaryocytes and/or production of platelets from megakaryocytes is indispensable for practical applications of in vitro platelet production technology.

Moreover, this technology may be applied to platelet production technology using embryonic stem cells (ES cells) that have attracted attention as a stem cell source that may solve a deficiency in stem cells (that is pointed out when using undifferentiated hematopoietic cells from the bone marrow or cord blood), or induced pluripotent stem cells (iPS cells) that are expected to solve an ethical problem and a rejection response with ES cells (see Patent Document 1, for example). Therefore, the technical impact may be very large.

PRIOR-ART DOCUMENT

Patent Document

Patent Document 1: JP-A-2007-89432

Non-Patent Document

Non-patent Document 1: Science, Vol. 301, 1531-1534 (2003)
Non-patent Document 2: Artificial Blood, Vol. 11, 193-199 (2003)
Non-patent Document 3: Blood, 91(1), 353-359 (1998)
Non-patent Document 4: YAKUGAKU ZASSHI, 121(9), 691-699 (2001)
Non-patent Document 5: Blood, 99(10), 3579-3584 (2002)
Non-patent Document 6: GENES & Dev., 17, 2864-2869 (2003)

SUMMARY OF THE INVENTION

Problems to be Solved by the Invention

An object of the present invention is to provide a novel method that effectively induces and produces platelets from undifferentiated hematopoietic cells (platelet precursor cells).

Means for Solving the Problems

The inventors considered that a method that merely adds a conventional chemical factor (chemical substance such as cytokine, sugar protein or the like) to a culture system has a limited effect on induction of platelets from undifferentiated hematopoietic cells, particularly release of platelets from megakaryocytes, and employed a technical approach that introduces a physical factor effective for platelet induction (i.e., scaffold structure) into the culture system, taking account of a hematopoietic microenvironment in the bone marrow of living body. The inventors investigated the effect of various polymer structures on production of megakaryocytes and/or platelets, and found that effective production of platelets and/or megakaryocytes from undifferentiated hematopoietic cells is induced by adding a certain porous support membrane that can three-dimensionally hold the cells to the culture system. The inventors also found that production of megakaryocytes and/or platelets from undifferentiated hematopoietic cells is effectively induced by adding a certain composite membrane in which a porous thin membrane that has a number of pores having a size of about several micrometers is stacked on a porous support membrane that can three-dimensionally hold the cells to the culture system.

Specifically, the present invention is as follows:

(1) An induction method comprising culturing platelet precursor cells in a culture solution in which a composite membrane is immersed and differentiating the platelet precursor cells into platelets and/or megakaryocytes, the composite membrane including a porous support membrane and a porous thin membrane which is stacked on at least one side of the porous support membrane, the porous thin membrane having a porosity of 5 to 80%, an average pore diameter D of 0.5 to 20 and a ratio ($\sigma d/D$) of a pore diameter standard deviation $\sigma d$ ($\mu m$) to the average pore diameter D of 0 to 0.6, and the porous support membrane having an average flow pore size of 1 $\mu m$ or more.

(2) An induction method comprising putting and culturing platelet precursor cells in an area of a composite membrane side, and differentiating the platelet precursor cells into platelets and/or megakaryocytes, the area being one of at least two areas divided by the porous thin membrane and forming by immersing the composite membrane in a culture solution, the composite membrane including a porous support membrane and a porous thin membrane which is stacked on at least one surface of the porous support membrane, the porous thin membrane having a porosity of 5 to 80%, an average pore diameter D of 0.5 to 20 $\mu m$, and a ratio ($\sigma d/D$) of a pore diameter standard deviation $\sigma d$ ($\mu m$) to the average pore diameter D of 0 to 0.6, and the porous support membrane having an average flow pore size of 1 $\mu m$ or more.

(3) The induction method according to (2), comprising applying a shear stress to the porous thin membrane by utilizing the culture solution in an area where the porous support membrane is not present, the area being one of the at least two areas divided by the porous thin membrane.

(4) The induction method according to any one of (1) to (3), wherein the porous thin membrane has an average thickness T of 0.5 to 30 $\mu m$, and a ratio ($\sigma t/T$) of a thickness standard deviation $\sigma t$ ($\mu m$) to the average thickness T of 0 to 0.5.

(5) The induction method according to any one of (1) to (4), wherein the porosity of the porous thin membrane is 10 to 80%.

(6) The induction method according to any one of (1) to (5), wherein the porosity, average pore diameter D, and an average thickness T of the porous thin membrane are 15 to 80%, 0.5 to 10 $\mu m$ and 0.5 to 15 $\mu m$, respectively.

(7) The induction method according to any one of (1) to (6), wherein the porous support membrane has an average flow pore size of 1 to 100 $\mu m$.

(8) The induction method according to any one of (1) to (7), wherein the porous support membrane is a nonwoven fabric.

(9) The induction method according to any one of (1) to (8), wherein the composite membrane has a structure that an organic polymer compound that forms the porous thin membrane is introduced into the porous support membrane.

(10) The induction method according to any one of (1) to (9), wherein the porous thin membrane has adjacent pores communicated each other inside the porous thin membrane.

(11) The induction method according to (8), wherein the nonwoven fabric has a structure formed by entangling and mixing at least one type of fine fibers having an average fiber diameter of 7 to 30 $\mu m$ with at least one type of ultrafine fibers having an average fiber diameter of 0.5 to 5 $\mu m$.

(12) The induction method according to (11), wherein the fine fibers are long fibers, and the ultrafine fibers are short fibers.

(13) The induction method according to any one of (1) to (12), wherein the porous thin membrane has through pores in the ratio to the total number of pores thereof is 20% or more.

(14) The induction method according to any one of (1) to (13), wherein the platelet precursor cells are hematopoietic stem cells.

(15) The induction method according to any one of (1) to (14), wherein the platelet precursor cells are bone marrow cells or cord blood-derived cells.

(16) The induction method according to any one of (15), wherein the cord blood-derived cells are mononuclear cells.

(17) The induction method according to any one of (1) to (16), comprising adding at least one cytokine to the culture solution.

(18) The induction method according to any one of (17), wherein the cytokine is selected from TPO, VEGF, and SCF.

(19) The induction method according to any one of (1) to (18), wherein the porous support membrane is filled with the platelet precursor cells in advance, and the composite membrane filled with the platelet precursor cells is immersed in the culture solution to culture the platelet precursor cells.

(20) Platelets and/or megakaryocytes produced by the method according to any one of (1) to (19).

(21) A platelet and/or megakaryocyte production apparatus comprising the composite membrane according to any one of (1) to (13), the apparatus inducing platelet precursor cells to differentiate into platelets and/or megakaryocytes by putting and culturing the platelet precursor cells in an area of the porous support membrane side, the area being one of at least two areas divided by the porous thin membrane and forming when immersing the composite membrane in a culture solution.

(22) A composite membrane comprising a porous support membrane and a porous thin membrane, the porous thin membrane being stacked on at least one side of the porous support membrane, (i) the porous thin membrane having a porosity of 5 to 80%, an average pore diameter D of 0.5 to 20 $\mu m$, and a ratio ($\sigma d/D$) of a pore diameter standard deviation $\sigma d$ ($\mu m$) to the average pore diameter D of 0 to 0.6, and (ii) the porous support membrane having an average flow pore size of 1 $\mu m$ or more, the composite membrane being used to induce platelet precursor cells to differentiate into platelets and/or megakaryocytes by culturing the platelet precursor cells in a culture solution in which the composite membrane is immersed.

Effects of the Invention

Platelets can be effectively produced in vitro using undifferentiated hematopoietic cells (platelet precursor cells) by utilizing the method that utilizes the composite membrane according to the present invention. Therefore, stable and safe transfusion alternative therapy that produces platelets in vitro in an amount corresponding to the current platelet transfusion, and returns the produced platelets in a living body is expected to be completed by utilizing the technology according to the present invention either alone or in combination with known technology.

MODES FOR CARRYING OUT THE INVENTION

Figure 1:
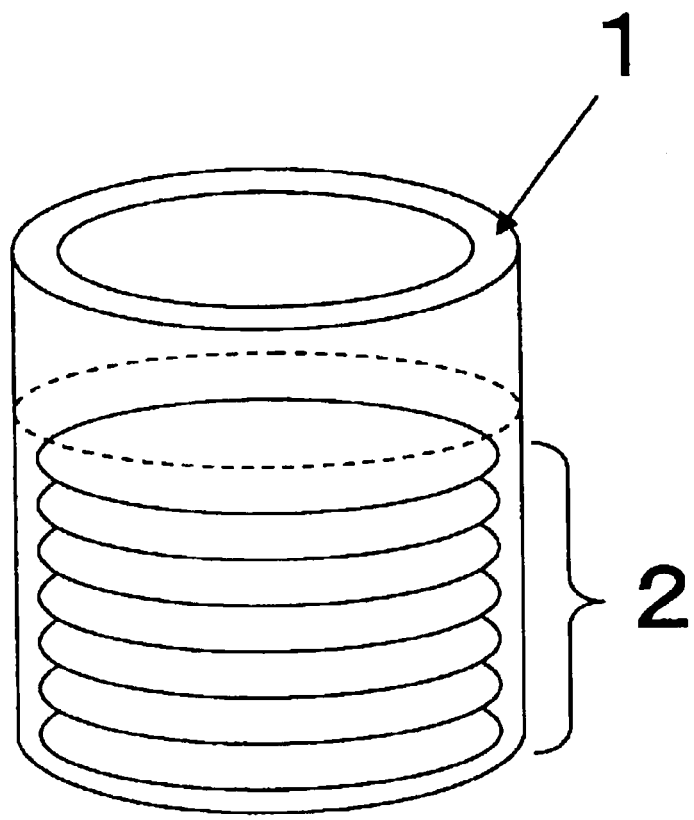
FIG. 1 is a schematic view showing an example of a culture method in which a plurality of composite membranes are disposed in a cylindrical culture vessel parallel to the bottom of the vessel.

The present invention is described in detail below.

Cell

The term "platelet precursor cell" used herein is a generic name for any undifferentiated cells that may differentiate into platelets. Examples of the platelet precursor cells include hematopoietic stem cells, hemopoietic precursor cells that are observed when hematopoietic stem cells differentiate into platelets, myeloid precursor cells, megakaryoblasts, megakaryocytes, and the like.

Further examples of the platelet precursor cells include adult stem cells, embryonic stem cells (ES cells), induced pluripotent stem cells (iPS cells), and a cell group that is observed when the cell group differentiates into platelets. Note that the platelet precursor cells are not limited to these cells.

The platelet precursor cells are at least one type of cells selected from the above undifferentiated cells. Specifically, only purified hematopoietic stem cells or megakaryocytes may be used as the platelet precursor cells, or two or more types of platelet precursor cells may be used in combination.

When using two or more types of platelet precursor cells, two or more types of purified cells may be mixed, or bone marrow cells or cord blood-derived cells including various undifferentiated cells in mixture state may be used. When using purified platelet precursor cells, it is necessary to use a large amount of purified cells in order to obtain a sufficient amount of platelets since megakaryocytes are not normally amplified, and hematopoietic stem cells also can be amplified in vitro only under special conditions. On the other hand, when using bone marrow cells or cord blood-derived cells as the platelet precursor cells, it is expected that the platelet precursor cells are amplified by culture since the bone marrow and the cord blood include undifferentiated cells that have various degrees of differentiation, and some of them may be relatively easily amplified in vitro. Therefore, the latter is an effective method in order to obtain a large amount of platelets. The bone marrow cell may be arbitrary cells derived from the bone marrow of an embryonic, neonatal, or adult. Bone marrow cells are collected from a mammal by a known method. It is preferable to use bone marrow cells immediately after collection. Note that frozen bone marrow cells may also be used.

Cord blood-derived cells are not particularly limited insofar as the cells are derived from a mammal, and mononuclear cells in cord blood are preferably. Cells are collected from cord blood by a known method.

When transplanting platelets obtained by the method according to the present invention to a mammal, it is preferable to use platelet precursor cells derived from the same species as the mammal to be transplanted. In particular, when transplanting platelets to a human, it is preferably to use human-derived cells with which the human leukocyte antigen (HLA) of the platelet precursor cells (bone marrow cell or cord blood-derived cells) almost coincides. When using the bone marrow, it is preferable to use autologous bone marrow.

Composite Membrane

The composite membrane used in the present invention has a structure in which a porous thin membrane and a porous support membrane are stacked. For example, the composite membrane may have a two-layer structure in which one porous thin membrane and one porous support membrane are stacked (i.e., porous thin membrane/porous support membrane structure), a three-layer sandwich structure in which the porous thin membrane is provided on each side of the porous support membrane (i.e., porous thin membrane/porous support membrane/porous thin membrane structure), or the like.

When the porous support membrane of the composite membrane is sandwiched with the two porous thin membranes, the properties such as average pore diameter, porosity and the like, the material, and the like of the porous thin membranes may be the same or different. When using the composite membrane having the three-layer sandwich structure, the platelet precursor cells can be confined in the membrane by introducing the platelet precursor cells into the porous support membrane through the cutting section of the membrane. It is preferable to use a structure formed by one porous thin membrane and one porous support membrane due to ease of production and the convenience of usage.

If the thickness of the composite membrane is too large, the workability of the composite membrane into various forms may decrease. Since the porous support membrane necessarily has a large thickness when the composite membrane has a large thickness, the amount of platelet precursor cells (particularly megakaryocytes) that are present adjacent to the porous thin membrane may decrease, so that the platelet induction efficiency may decrease. The thickness of the composite membrane is preferably 5 mm or less, more preferably 3 mm or less, and most preferably 1 mm or less. If the thickness of the composite membrane is too small, the handling capability and the workability of the composite membrane may decrease. Therefore, the thickness of the composite membrane is preferably 1 µm or more, more preferably 5 µm or more, and most preferably 10 µm or more.

The porous thin membrane of the composite membrane is described below.

The shape of the pores of the porous thin membrane when viewed in the direction perpendicular to the surface of the porous thin membrane of the composite membrane is not particularly limited, but is preferably a circle in the consideration of the easy passing ability of the cytoplasm of platelets or megakaryocytes. The term "circle" used herein includes an ellipse in addition to a perfect circle.

The porosity of the porous thin membrane determined from a micrograph of the surface of the porous thin membrane is 5 to 80%. The porosity of the porous thin membrane is preferably 10 to 80%, more preferably 15 to 80%, still more preferably 20 to 70%, particularly preferably 25 to 70%, and most preferably 30 to 60%. If the porosity of the porous thin membrane is less than 5%, the induction efficiency of platelets from megakaryocytes may decrease. When putting and culturing the platelet precursor cells in an area of the porous support membrane side among at least two areas partitioned by the porous thin membrane, only produced platelets pass through the pores of the porous thin membrane, and can be collected. In this case, the separation efficiency may decrease if the porosity of the porous thin membrane is less than 5%.

In the present invention, differentiation induction of cells can be promoted by applying a shear stress caused by the flow of the culture solution that imitates the blood flow in the bone marrow to the platelet precursor cells. If the porosity of the porous thin membrane is too low, a shear stress may be scarcely perceivable by the cells in the porous support membrane even if the cells are cultured by utilizing the culture solution in an area where the porous support membrane is not disposed while applying the shear stress to the porous thin membrane. Therefore, it is disadvantageous for the porosity of the porous thin membrane to be less than 5%. If the porosity of the porous thin membrane is more than 80%, the strength of the porous thin membrane may decrease to a large extent, so that the porous thin membrane may be damaged due to break, crack or the like.

The average pore diameter D of the porous thin membrane is 0.5 to 20 µm, preferably 1 to 15 µm, more preferably 1 to 10 µm, and most preferably 1 to 5 µm. If the average pore diameter D of the porous thin membrane exceeds 20 µm, the induction efficiency of platelets from megakaryocytes may decrease. When putting and culturing the platelet precursor cells in an area of the porous support membrane side, only produced platelets pass through the pores of the porous thin membrane, are separated in an area of the opposite side and are collected. In this case, if the average pore diameter D of the porous thin membrane exceeds 20 µm, most of the platelet precursor cells also pass through the pores of the porous thin membrane so that the porous thin membrane may not exert the performance of size-separating platelets.

If the average pore diameter D of the porous thin membrane is less than 0.5 µm, the induction efficiency of platelets from megakaryocytes may decrease. Moreover, produced platelets may not pass through the porous thin membrane, and produced platelets may thus not be separated. If the average pore diameter D of the porous thin membrane is too small, similar to the low limit of the above porosity, a shear stress may be scarcely perceivable by the cells in the porous support membrane even if the platelet precursor cells are cultured while applying a shear stress to the porous thin membrane. Therefore, it is desirable for the average pore diameter D of the porous thin membrane to be not less than 0.5 µm.

The ratio (σd/D) of the pore diameter standard deviation σd (μm) to the average pore diameter D of the porous thin membrane is preferably 0 to 0.6, more preferably 0 to 0.5, particularly preferably 0 to 0.4, and most preferably 0 to 0.3. If the ratio (σd/D) exceeds 0.6, the induction efficiency of platelets from megakaryocytes may be unstable due to a broad pore diameter distribution, and the produced platelet size separation efficiency may also decrease.

The composite membrane used in the present invention has a structure in which the porous thin membrane is stacked on at least one surface of the porous support membrane. It is practically preferable that the porous thin membrane be reliably bonded to the porous support membrane, and both are not easily separated. It is preferable that the porous thin membrane be bonded to the porous support membrane over a wide range of the contact surface of the porous thin membrane with the porous support membrane surface. Note that the porous thin membrane may be bonded to the porous support membrane only at the four corners or periphery of the composite membrane. In the latter case, the contact area structure is not particularly limited, the porous thin membrane may be bonded to the porous support membrane using a known adhesive (that does not adversely affect culture due to an eluted substance or the like), or may be thermally bonded to the porous support membrane.

When the porous thin membrane is uniformly bonded to the porous support membrane over a wide range of the contact surface in the stacking plane of the both membranes while minimizing clogging of the pores of the porous thin membrane, the adhesive strength increases, and the induction efficiency of platelets from the platelet precursor cells is expected to increase since the porous support membrane and the porous thin membrane are sufficiently bonded or positioned adjacently. Such an adhesion structure is thus particularly preferable.

When bonding the porous thin membrane to the porous support membrane using an adhesive, a large number of pores of the porous thin membrane and the porous support membrane may unpreferably be clogged. It is preferable that part of the porous thin membrane is introduced into the porous support membrane from at least part of the porous support membrane surface that is positioned adjacent to the porous thin membrane. This configuration of the introduction means that when observing the surface of the porous thin membrane of the composite membrane using an electron microscope, the porous thin membrane is introduced into depressions and the like of the porous support membrane (voids between fibers or fiber entanglement areas when the porous support membrane is formed of nonwoven fabric), so that the pores of the porous thin membrane are deformed, or clogged on the surface of the porous thin membrane of the porous support membrane side (non-through structure).

When the porous thin membrane is uniformly bonded to the porous support membrane over a wide range of the contact surface in the stacking plane of the both membrane, since some of the pores of the porous thin membrane are closed by the porous support membrane, it is very rare that all of the pores of the porous thin membrane are open. The ratio of the number of through pores which the porous thin membrane has to the total number of pores of the porous thin membrane is preferably 20% or more, more preferably 30% or more, still more preferably 40% or more, and most preferably 50% or more in the composite membrane. If the ratio of the number of through pores is less than 20%, the induction efficiency of platelets from megakaryocytes, or the produced platelet separation efficiency may decrease.

Note that the "through pore(s)" of the porous thin membrane refer to pores through which the structure of the opposite porous support membrane (the structure of the porous support membrane that is not bonded to the porous thin membrane, or voids formed by the pores of the porous support membrane) can be seen when observing from the surface of the porous thin membrane side of the composite membrane using a microscope (electron microscope).

The average thickness T of the porous thin membrane can be measured by observing the cross section of the composite membrane using a microscope (electron microscope), and is 0.5 to 30 μm, preferably 0.5 to 20 μm, more preferably 1 to 15 μm, particularly preferably 1 to 10 μm, and most preferably 1 to 7 μm. If the average thickness T is less than 0.5 μm, the strength of the membrane may decrease to a large extent, so that the membrane may break during use. If the average thickness T of exceeds 30 μm, the induction efficiency of platelets from megakaryocytes, or the separation efficiency of the produced platelets may decrease. When culturing the platelet precursor cells while applying a shear stress to the porous thin membrane by utilizing the culture solution present in an area where the porous support membrane is not disposed, in order to be perceivable the shear stress by megakaryocytes (platelet precursor cells) present in the porous support membrane, the average thickness T of the porous thin membrane is smaller the better.

The ratio (σt/T) of the thickness standard deviation σt (μm) to the average thickness T of the porous thin membrane is preferably 0 to 0.5, more preferably 0 to 0.4, and particularly preferably 0 to 0.3. If the ratio (σt/T) exceeds 0.5, the induction efficiency of platelets from megakaryocytes may be unstable due to a broad thickness distribution, and the produced platelet size separation efficiency may also decrease.

When the porosity, the average pore diameter D, the pore diameter standard deviation σd, and the ratio of the number of the through pores of the porous thin membrane cannot be specified by the methods described herein, such a porous thin membrane does not fall within the range of the porous thin membrane according to the present invention. For example, the above items can hardly be specified by the methods described herein when using a nonwoven fabric or a porous body that is mainly obtained by a phase separation method and has communicating pores in a three-dimensional network. Therefore, such a nonwoven fabric or a porous body is clearly different from the porous thin membrane according to the present invention.

The internal structure of the porous thin membrane is not particularly limited. It is preferable that each pore communicates with the adjacent pores inside the membrane. The pores may have a linear tubular structure or a bent tubular structure. It is preferable that the pore structure expands spherically inside the membrane from the viewpoint of the entrance of the megakaryocyte cytoplasm and the pass-through efficiency of the produced platelet, but particularly not limited thereto.

A membrane structure in which each pore communicates with the adjacent pores each other inside the membrane. Although the method of producing a membrane structure in which the pore expands spherically inside the membrane is particularly not limited, for example, such a porous thin membrane may be produced by a known method that utilizes minute water droplets as a template (see Thin Solid Films, 327-329, 854 (1998), for example). A composite porous membrane and a method of producing the same utilizing this technology are disclosed in WO2005/014149A1. Specifically, the composite porous membrane disclosed in WO2005/014149A1 is one of the most suitable composite membranes as a configuration thereof used in the platelet induction method according to the present invention.

A porous thin membrane in which the pores have a linear tubular structure may be produced by using a method applying radiation to various thin polymer films and then etching the thin polymer films, a photolithographic method, a nanoimprint lithographic method using a mold having a protrusion structure, or the like.

The porous thin membrane may be formed of an organic material or an inorganic material. It is preferable that the porous thin membrane be formed of an organic polymer compound since the membrane can be easily formed. Examples of the organic polymer compound include, but are not limited to, polylactic acid, polyhydroxyacetic acid, polycaprolactone, polyesters such as polyethylene adipate, polyurethanes, poly(meth)acrylates, polyvinyl acetals, polyamides, polystyrenes, polysulfones, cellulose derivatives, polyphenylene ethers, polyethersulfones, polycarbonates, polyvinyl alcohol, an ethylene-vinyl alcohol copolymer, or polymer alloys or blends of two or more of the above polymers, a copolymer of monomers that form the above polymers, and the like.

The porous support membrane is described below.

The porous support membrane supports and reinforces the porous thin membrane, and take on the function of providing the composite membrane with sufficient mechanical strength. Since the porous support membrane must also take account of the function as a scaffold material supporting the platelet precursor cells in addition to the sufficient mechanical strength, it is preferable that the porous support membrane have a pore size suitable for allowing a suspended cell solution to pass through the porous support membrane, allowing cells to be introduced into the inside of the porous support membrane, and three-dimensionally holding the introduced cells. The porous support membrane has communicating pores having an average flow pore size of 1 µm or more, preferably 1 to 100 µm, and more preferably 1 to 50 µm. If the average flow pore size is less than 1 µm, it may be difficult to introduce the platelet precursor cells into the inside of the porous support membrane and the porous thin membrane surface (or vicinity thereof) of the porous support membrane side, so that the platelet precursor cells may not be three-dimensionally cultured, or platelets may not be induced utilizing the properties of the porous thin membrane. If the average flow pore size exceeds 100 µm, the porous thin membrane may not be sufficiently supported, so that the porous thin membrane may easily break. Moreover, the porous support membrane may not exert the function as a three-dimensional hold or scaffold for the platelet precursor cells.

The term "communicating pore" refers to a pore that is formed from one surface to the other surface of the porous support membrane. The shape of the communicating pores on the surface of the membrane and the structure of the communicating pores inside the membrane are not limited insofar as a liquid or a gas can pass through the communicating pores.

If the thickness of the porous support membrane is too large, it may be difficult to process the composite membrane into various forms. Moreover, the platelet precursor cells may not be sufficiently introduced into the porous support membrane. The thickness of the porous support membrane is preferably 5 mm or less, more preferably 3 mm or less, and most preferably 1 mm or less. If the thickness of the porous support membrane is too small, the porous support membrane may not serve as a support layer. Therefore, the thickness of the porous support membrane is preferably 1 µm or more, more preferably 5 µm or more, and most preferably 10 µm or more.

Specific examples of the porous support membrane include a nonwoven fabric produced using natural fibers, synthetic polymer fibers, regenerated polymer fibers, inorganic fibers represented by glass fibers, organic/inorganic composite fibers, or the like, and a porous body (porous membrane) that has communicating pores formed in a three-dimensional network, and is obtained by thermally melting an organic polymer material, dissolving in a solvent, plasticizing the solution using a plasticizer, and forming the resultant using a foaming method, a phase separation method (thermally induced phase separation method or wet phase separation method), a drawing method, a sintering method, or the like, for example. A woven fabric or a knitted fabric produced using natural fibers, synthetic polymer fibers, regenerated polymer fibers, glass fibers, organic/inorganic composite fibers, or the like, various mesh products produced using an organic material, an inorganic material, a metal material, or a hybrid material thereof also can be given.

The porous support membrane is required to absorb a suspended cell solution (culture solution) including the platelet precursor cells (several to several tens of µm) so that the platelet precursor cells are introduced into the porous support membrane, and have an excellent function of three-dimensionally holding the introduced cells. Therefore, it is preferable that the porous support membrane be easily designed so as to have a relatively large pore size (about several to several tens of µm) and porosity corresponding to the cell size. Since a nonwoven fabric is provided a wide range of structural design, a nonwoven fabric is particularly preferably used as the porous support membrane. It is particularly preferable to use an organic polymer nonwoven fabric that has a plenty of variation in pore size and weight per unit area (metsuke), and exhibits excellent workability.

Examples of the organic polymer nonwoven fabric material include polyalkylene terephthalates, polycarbonates, polyurethanes, poly(meth)acrylates, polyacrylonitrile, polyvinyl alcohol, an ethylene-vinyl alcohol copolymer, polyvinyl acetal, polyesters, polyamides, polystyrenes, polysulfones, cellulose and cellulose derivatives, polyphenylene ethers, polyethylene, polypropylene, polyvinyl fluoride, polyvinyl chloride, polyvinylidene fluoride, a copolymer of monomers that form the above polymers, an alloy or blend of one or more of the above polymers, and the like, but not limited thereto.

When using a nonwoven fabric as the porous support membrane, the nonwoven fabric may be inhibited the function of passing through the pores of the porous thin membrane if the average fiber diameter of the nonwoven fabric is too large. If the average fiber diameter of the nonwoven fabric is too small, the strength of the nonwoven fabric itself may decrease, so that the resulting composite membrane may exhibit insufficient strength. The average fiber diameters of the nonwoven fabric is preferably 0.1 to 50 µm, more preferably 0.5 to 30 µm, still more preferably 1 to 15 µm, and most preferably 1 to 5 µm.

If the weight per unit area of the nonwoven fabric is too high, cells may be inhibited to pass through the pores of the porous thin membrane, or it may be difficult to introduce the platelet precursor cells into the nonwoven fabric. If the weight per unit area of the nonwoven fabric is too low, the porous thin membrane may not be sufficiently supported or reinforced, or the resulting composite membrane may exhibit insufficient strength. The weight per unit area of the nonwoven fabric is preferably 5 to 250 $g/m^2$, more preferably 10 to 150 $g/m^2$, and still more preferably 10 to 100 $g/m^2$.

The composite membrane used in the present invention is required the following two conditions:

(1) cells can be easily introduced into the porous support membrane and the porous thin membrane surface of the porous support membrane side (or vicinity thereof) by immersing the composite membrane in a suspended cell solution (culture solution), or passing the suspended cell solution through the composite membrane from the porous support membrane side (described later), and (2) the porous thin membrane does not break, and is uniformly bonded to the porous support membrane while maintaining an appropriate shape. In order to satisfy the above requirements, it is preferable to use a composite membrane produced using as the porous support membrane a nonwoven fabric having a structure obtained by entangling and mixing at least one type of fine fibers and at least one type of ultrafine fibers by the method disclosed in WO2005/014149A1.

The term "fine fibers" refers to fibers having an average diameter of 7 to 30 µm, preferably 10 to 25 µm, and particularly preferably 13 to 20 µm, from the viewpoint of maintaining the mechanical strength of the entire nonwoven fabric and ensuring excellent integral formability of the porous thin membrane. If the diameter of the fine fibers is smaller than 7 µm, the handling capability of the composite nonwoven fabric or the entire composite membrane may decrease due to insufficient mechanical strength. On the other hand, if the diameter of the fine fibers exceeds 30 µm, the contact (bonding) area with the porous thin membrane may increase, so that cells may be severely inhibited to pass through the pores of the porous thin membrane. Moreover, the porous thin membrane integrally formed on (bonded to) the surface of the composite nonwoven fabric may undergo significant undulation due to minute elevations and depressions caused by the large fiber diameter of the composite nonwoven fabric surface, so that cracks may occur on the membrane surface (particularly an area along the fibers), and the membrane may easily break. The fine fibers may be long fibers or short fibers. Since the fine fibers with a relatively small weight per unit area mainly provide the composite nonwoven fabric and the composite membrane with mechanical strength, the fine fibers are preferably long fibers.

The term "ultrafine fibers" refers to fibers having an average diameter of 0.5 to 5 µm, preferably 1 to 5 µm and particularly preferably 1 to 3 µm. If the diameter of the ultrafine fibers is smaller than 0.5 µm, the ultrafine fibers may easily break due to insufficient strength. As a result, fiber waste may be produced during forming the membrane or using the composite membrane, the ultrafine fibers may not be preferably used for some application. If the diameter of the ultrafine fibers exceeds 5 µm, it becomes close to the diameter of the fine fibers, so that the meaning of introducing the ultrafine fibers may become obscure. Moreover, since the fine fibers and the ultrafine fibers are unlikely to entangle to each other, a structure in which the fibers are sufficiently entangled and mixed may not be obtained, so that the effect of using the fine fibers and the ultrafine fibers may be reduced. The ultrafine fibers may be long fibers or short fibers. It is preferable that the ultrafine fibers are easily entangled with the fine fibers, and easily introduced into the fine fiber area, therefore, the ultrafine fibers are preferably short fibers.

The ratio of the weight of the ultrafine fibers to the total weight of the fine fibers and the ultrafine fibers that form the composite nonwoven fabric is not particularly limited, but is preferably 1 to 50 wt %, more preferably 5 to 40 wt %, and particularly preferably 10 to 30 wt %. If the ratio is less than 1 wt %, the effect of using the ultrafine fibers may be insufficient. If the ratio exceeds 50 wt %, the mechanical strength of the composite nonwoven fabric may decrease.

In the composite nonwoven fabric the structure obtained by entangling and mixing the fine fibers and the ultrafine fibers refers to a structure in which the ultrafine fibers are entered into the nonwoven fabric layer formed by the fine fibers. Such a structure may be confirmed using an optical microscope (particularly a stereoscopic microscope) or an electron microscope. The degree of entering the ultrafine fibers into the fine fiber layer is not particularly limited insofar as the effects of the present invention can be achieved. It is particularly preferable to use a structure in which the ultrafine fibers are sufficiently entered into the fine fiber layer (i.e., the gaps between the fine fibers are evenly filled with the ultrafine fibers).

A composite nonwoven fabric having a structure in which the ultrafine fibers are entered into the nonwoven fabric layer may be obtained by various methods. For example, such a composite nonwoven fabric may be produced by layering a fine fiber nonwoven fabric (long fiber nonwoven fabric) produced by a spunbond method and ultrafine fiber nonwoven fabric (short fiber nonwoven fabric) produced by a melt blow method, and stacking the nonwoven fabrics by a thermocompression bonding method using a heat embossing roll. When using such a method, however, the ultrafine fibers may not be sufficiently entered into the fine fiber layer. A nonwoven fabric in which the ultrafine fibers are sufficiently entered into the fine fiber layer may be obtained by the process of producing a spunbond long fiber nonwoven fabric disclosed in WO2004/094136, wherein melt-blown ultrafine fibers are directly blown onto a long fiber web including a number of continuous long fibers that is melt-spun and deposited on a moving collector. Specifically, a first deposited long fiber web (SW1) consisting of many continuous long fibers is melt spun on a moving collector face. A melt-blown ultrafine fiber web (MW) is directly blown on the entire face of the first web. Similarly, a second deposited long fiber web (SW2) consisting of many continuous long fibers is further deposited on the entire face of the MW layer, so that a sheet-like stacked SMS web is formed. The MW layer is integrated during the step of thermocompressively bonding in a sandwiched state, and a composite nonwoven fabric structure in which the melt-blown ultrafine short fibers are sufficiently entered into the spunbond fine long fiber layer, is obtained. Such a composite nonwoven fabric is particularly preferable structure in the present invention.

The composite membrane used in the present invention may be subjected to surface modification treatment such as hydrophilic treatment in order to improve hydrophilicity and protein non-absorption properties, and control cellular adhesiveness, for example.

Specific examples of the surface modification treatment (particularly hydrophilic treatment) method include (a) a method of introducing a desired hydrophilic functional group or the like into a functional group present on the surface of the composite membrane by a polymer reaction, (b) a method of applying electron beams or γ-rays to the composite membrane to produce radicals, and graft-polymerizing a monomer having the desired hydrophilic functional group therewith, (c) a method of entering a necessary initiator group into the composite membrane, and then graft-polymerizing a monomer having the desired functional group by various living polymerization (e.g., living radical polymerization or living anion polymerization) that is conducted by optionally adding a catalyst or the like, (d) a method of coating the composite membrane with a polymer having the desired functional group by a dipping method or a spray method, and the like. Particularly the coating method (d) is preferable since the type and the amount of functional group to be induced, and the polymerization chain distribution, and the like can be easily designed when synthesizing the coating polymer, and the coating process is simple and increases productivity. The details of the coating method are disclosed in WO2005/014149A1.

The coating agent may be one, or two or more of known synthetic hydrophilic polymers disclosed in WO2005/014149A1, and known natural polymers such as collagen, fibronectin, vitronectin, proteoglycan, glycosaminoglycan, gelatin, lectin, polylysine and the like.

Culture Method

A culture method using a composite membrane having a two-layer structure in which one porous thin membrane and one porous support membrane are stacked is described below.

In the present invention, the platelet precursor cells are induced to platelets by culturing the platelet precursor cells in a culture solution in which the composite membrane is immersed (i.e., culturing the platelet precursor cells in a state in which the composite membrane coexists with the platelet precursor cells).

As the method of coexisting the composite membrane and the platelet precursor cells in a culture solution, for example,
(1) a method in which the composite membrane is immersed in a culture solution including the platelet precursor cells,
(2) a method in which a culture solution including the platelet precursor cells is put into a culture vessel in which the composite membrane has been placed in advance, or
(3) a method in which the porous support membrane is filled with the platelet precursor cells in advance, and immersed in a culture solution, but not particularly limited thereto.

It is considered that the platelet precursor cells in the culture solution are efficiency induced to differentiate into megakaryocytes by three-dimensional culture in a state in which the platelet precursor cells are held inside the porous support membrane, in addition the megakaryocytes are present near the porous thin membrane stacked on the porous support membrane and detect the structure of the porous thin membrane so that the platelet induction efficiency increases. Therefore, the above method (3) is preferable.

As described above (3), though the method of filling the platelet precursor cells in the porous support membrane may not be limited, for example, as such a method, a method of passing a suspended cell solution including the platelet precursor cells through the composite membrane from the porous support membrane surface to the porous thin membrane side can be given. In this case, most of the liquid components are discharged from the porous thin membrane, and only the cells are captured by the surface (or vicinity thereof) of the porous thin membrane adjacent to the porous support membrane. When the liquid components are discharged at a low rate, the discharge side (porous thin membrane side) may be decompressed, or the introduction side (porous support membrane side) may be pressurized. The discharge of the liquid components can be easily accelerated by bringing a water absorber (e.g., water-absorbing sheet or the like) in contact with the porous thin membrane of the discharge side.

The shape of the composite membrane immersed in the culture solution is not particularly limited. A flat membrane may be directly immersed in the culture solution as in the flat shape, or may be pleated or rolled, and disposed and immersed in the culture solution.

Figure 2:
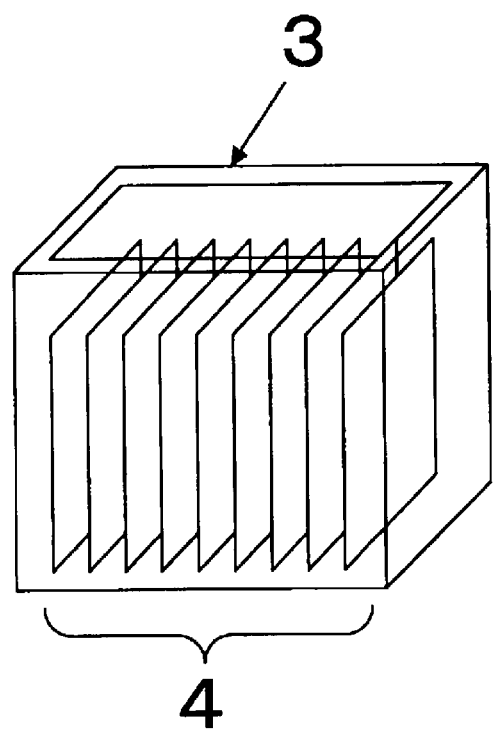
FIG. 2 is a schematic view showing an example of a culture method in which a plurality of composite membranes are disposed in a rectangular parallelepiped culture vessel perpendicularly to the bottom of the vessel.

When directly immersing a flat membrane in the culture solution while maintaining the flat shape, the flat membrane may be cut into any shape that fits the shape of a culture vessel, and one or more membranes thus cut may be disposed parallel with, or perpendicularly to, the bottom face of the vessel and immersed. FIG. 1 is a schematic view showing a state in which a plurality of flat membranes are disposed parallel with the bottom face of the vessel, and FIG. 2 is a schematic view showing a state in which a plurality of flat membranes are disposed perpendicularly to the bottom face of the vessel. When disposing the flat membranes parallel with the bottom face of the vessel as shown in FIG. 1), the cells in the porous support membrane can be moved closer to the vicinity of the porous thin membrane due to gravity by disposing the flat membranes (composite membranes) so as to face the porous thin membrane surface to the bottom face of the vessel, so that the platelet precursor cells easily detect the structure of the porous thin membrane, and it is advantageous in the platelet induction efficiency.

The larger the area of the composite membrane immersed in the culture solution the better, when immersing the composite membranes into the culture solution even in any shape. If the area of the composite membrane immersed in the culture solution increases, the probability that the platelet precursor cells are present inside the porous support membrane increases and the probability that the platelet precursor cells are present near the porous thin membrane also increases, so that the platelet induction efficiency increases. However, if the area of the composite membrane (the volume of the composite membrane) immersed in the culture solution is too large, the amount of culture solution that can be put into the culture vessel decreases, that is, the amount of nutrients necessary for the cells decreases, and it may be fear that oxygen cannot be provided to the entire culture solution sufficiently. Therefore, it is necessary to determine the appropriate area of the composite membrane immersed in the culture solution corresponding to the purpose of the culture by placing appropriate spacers between plural sheets of the composite membranes.

In the present invention, the platelet precursor cells are induced to differentiate into platelets by putting and culturing the platelet precursor cells in an area of the porous support membrane side, the area being one of at least two areas divided by the porous thin membrane and formed when immersing the composite membrane in the culture solution.

The "area" of the above two areas refers to an area for culturing the cells, the porous thin membrane of the composite membrane plays a role of dividing to the two areas. Specifically, when a composite membrane in which the porous thin membrane is stacked on one side of the porous support membrane is placed in the culture solution, two areas are formed by one sheet of the porous thin membrane of a border. When a composite membrane having a three-layer sandwich structure in which the porous thin membranes are stacked on both sides of the porous support membrane is placed in the culture solution, three areas are formed by the two porous thin membranes in the composite membrane. In this case, the area between the two porous thin membranes, that is, porous support membrane itself is the area of the porous support membrane side.

Although the method of forming at least two areas divided by the porous thin membrane while immersing the composite membrane may not be limited, for example, the following method may be given.

Specifically, the composite membrane used in the present invention is cut into quadrangular shapes having an identical size. A bag-shaped composite membrane is produced by superposing the resulting composite membranes side by side so that the porous support membranes are positioned in facing orientation relative to one another, and heat-sealing three sides of the composite membranes. The bag-shaped composite membrane is disposed in the culture solution (the opening of the bag is positioned above the liquid surface or sealed) so that two adjacent areas divided by the porous thin membrane are formed inside and outside the bag-shaped composite membrane. The bag-shaped composite membrane is charged with a suspended cell solution including the platelet precursor cells, and the cells are filtered to fill the porous support membrane with the cells. The bag-shaped composite membrane is then immersed in the culture solution. When disposing two bag-shaped composite membranes in the culture solution, three culture areas are obtained by dividing by the porous thin membranes. When disposing three bag-shaped composite membranes in the culture solution, four culture areas are obtained by dividing by the porous thin membranes. FIG. 2 also schematically shows a state in which plural sheets of bag-shaped composite membranes are disposed in the culture solution.

At least two areas divided by the porous membrane may also be formed in the culture solution by assembling a culture apparatus (platelet production apparatus) using the composite membranes and various members in combination.

Figure 3:
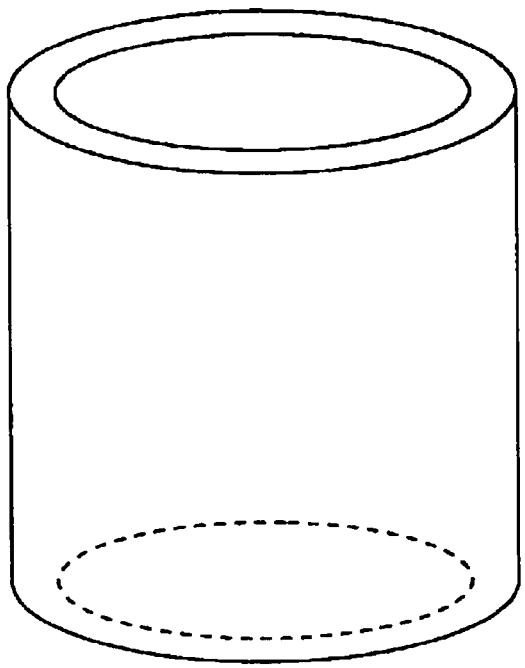
FIG. 3 is a schematic view showing an example of a tubular body that forms a cup-shaped vessel.
Figure 4:
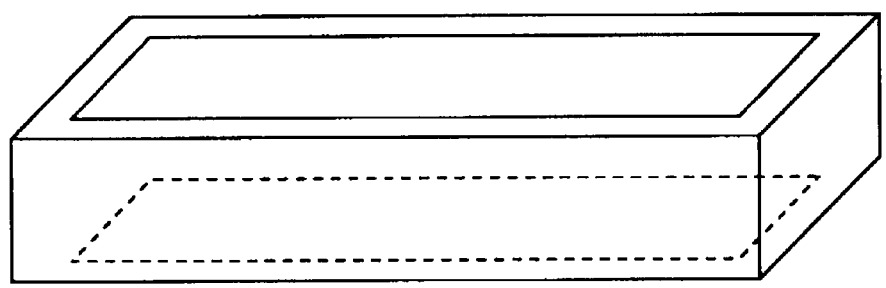
FIG. 4 is a schematic view showing an example of a tubular body that forms a cup-shaped vessel.

A basic structure of the culture apparatus includes in combination with a cup-shaped vessel produced by bonding the composite membrane to one end face of a tubular body made of glass or plastic, and a vessel that can receive the cup-shaped vessel and the culture solution. Though the form and the size of the tubular body are not particularly limited, for example, a tubular body shown in FIG. 3 or 4 may be used. Either the porous support membrane or the porous thin membrane of the composite membrane may be bonded to one end face of the tubular body depending on the application and the objective. However, as described above when introducing the platelet precursor cells into the composite membrane from the porous support membrane side, it is convenient to bond the porous support membrane to the tubular body.

When culturing the platelet precursor cells in a state sealed from the atmosphere in order to prevent contamination of the culture system, the cup-shaped vessel must be integrated with the vessel that can receive the cup-shaped vessel and the culture solution. For example, a closed-type culture apparatus may be produced by connecting a pipe or the like to the inlet and the outlet of a basic unit shown in FIG. 5. The basic unit shown in FIG. 5 includes a platelet precursor cell inlet (5), a culture solution inlet (6), a produced platelet suspension outlet (7), a composite membrane (8), a cup-shaped vessel (9), a culture solution vessel (10), a housing (11), and a stirrer (12). Note that the basic unit may optionally include an additional inlet or the like. A magnetic stirrer or the like may be provided on the lower side of the apparatus, and rotated the stirrer so that a shear stress due to fluid may be applied to the platelet precursor cells (particularly megakaryocytes) present in the porous support membrane through the porous thin membrane.

When partitioning the culture solution using the porous thin membrane as described above, putting and culturing the platelet precursor cells in the area of the porous support membrane side, only platelets produced from the platelet precursor cells move to the opposite area through the pores of the porous thin membrane by controlling the pore size of the porous thin membrane, so that the produced platelets can be easily collected depending on the size.

Figure 5:
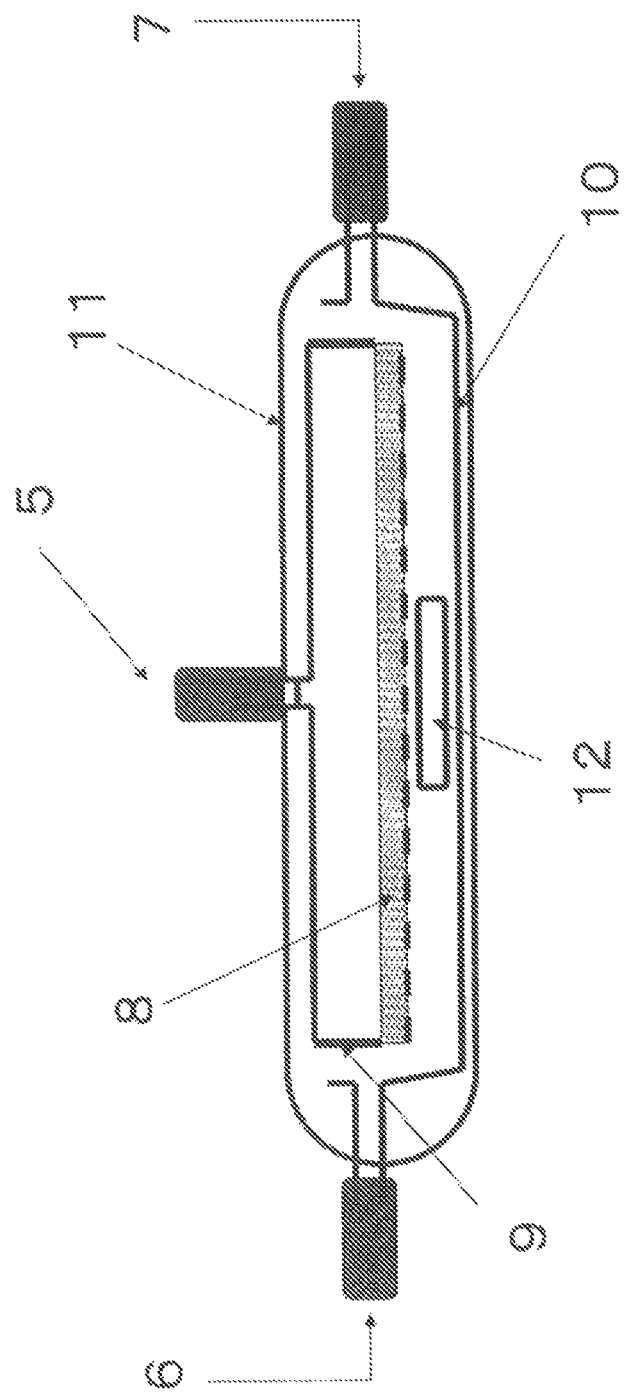
FIG. 5 is a schematic view showing an example of a basic unit of a closed-type culture apparatus.

In particular, the closed-type culture apparatus shown in FIG. 5 allows platelets to be produced from megakaryocytes in the area where the porous support membrane is disposed, and enter into the culture solution vessel side through the pores of the porous thin membrane, so that the produced platelets can be continuously collected while circulating and collecting the culture solution. In this case, the platelet production efficiency is thought to be decrease, if the platelet precursor cells (particularly megakaryocytes) are mixed into the culture solution in the culture vessel. Therefore, it is one of important functions that the porous thin membrane size-selectively prevents cells other than platelets from mixing. There particularly occurs no trouble even when producing platelets using own hematopoietic stem cells (platelet precursor cells). However, when producing platelets using hematopoietic stem cells (platelet precursor cells) collected from another person having different leukocyte antigens, or inducing the production of platelets using ES cells or iPS cells as the stem cell source, it is very dangerous that cells having a cell nucleus other than that of the autologous cells are mixed in during transplantation. There is a method of selectively collecting only platelets from whole blood by centrifugation. However, it is advantageous to inhibit passing nucleated cells through the membrane as much as possible in order to prevent the risk of contamination. Therefore, it is one of important functions that only the platelets selectively pass through the porous thin membrane.

One or more of porous support membrane may be further stacked on the porous support membrane side of the composite membrane. This increases the three-dimensional culture area for the platelet precursor cells introduced into the porous support membrane by further stacking a porous support membrane. In this case, the additional porous support membrane may be the same as or different from the first porous support membrane of the composite membrane.

When performing the platelet induction method according to the present invention, the culture solution may be in a stationary state, or may also be preferably circulated or stirred. This produces an effect to uniformly supply oxygen and nutrients to all of the cells in the culture solution. Moreover, induction of cell differentiation (particularly release of platelets from megakaryocytes) is promoted by applying a shear stress that imitates the blood flow through the bone marrow of the living body to the platelet precursor cells.

In particular, when putting and culturing the platelet precursors in an area of the porous support membrane side (particularly inside the porous support membrane) that is one of at least two areas formed by immersing the composite membrane in the culture solution, and divided by the porous thin membrane, the platelet precursor cells detect a shear stress due to fluid through the pores of the porous thin membrane by applying a shear stress to the porous thin membrane utilizing the culture solution in an area where the porous support membrane is absent, so that platelet release is promoted. A preferable culture method may be provided. The method of applying a shear stress to the porous thin membrane by utilizing the culture solution present in an area where the porous support membrane is absent does not particularly limited. For example, a shear stress may be applied utilizing the culture solution by stirring the culture solution, or moving, rotating, or vibrating the porous thin membrane (composite membrane) to give flowability. Note that aggregation or activation of produced platelets may occur if the shear stress is applied too much.

The cell culture solution may be used a culture solution normally used for culturing mammalian cells, such as a DMEM culture solution, an MEM culture solution, an α-MEM culture solution, a RPMI culture solution, a DMEM/F12 culture solution or the like. An appropriate amount of bovine serum or human serum may be added to the culture solution. The amount of serum added to the culture solution is appropriately determined depending on the origin and the type of cells. Serum is preferably added in an amount of about 0 to 20%, and more preferably about 5 to 10%. A serum-free culture solution such as Nutridoma (manufactured by Boehringer) may be used instead of serum.

The culture period varies depending on the type of platelet precursor cells, and may thus not be limited. For example, when using hematopoietic stem cells as the platelet precursor cells, since a period for inducing the hematopoietic stem cells to differentiate into megakaryocytes is necessary, about one week of the culture period is required. When using megakaryocytes as the platelet precursor cells, the culture period is preferably 1 to 4 days, and more preferably 1 or 2 days. In any cases, taking account of the short life of platelets, it is preferable to determine the culture period that the produced platelets are not inactivated by monitoring the platelet production start time.

The culture conditions such as temperature, $CO_2$ and the like are appropriately set depending on the properties of the cells. The cells are normally cultured at 4 to 6% $CO_2$ and 33 to 37° C., and preferably at about 5% $CO_2$ and about 37° C. A cytokine that promotes differential proliferation of cells may be appropriately added to the culture solution during the culture. Examples of the cytokine include EGF family cytokines, such as EGF, TGF-α, HB-EGF, FGF, HGF and the like, TGF-β family cytokines such as TGF-β and the like, IL family cytokines such as LIF and the like, VEGF family cytokines such as VEGF-A and the like, PDGF family cytokines such as PDGF-AB, PDGF-BB and the like, Ephrin family cytokines such as ephrins B and the like, stem cell factor (SCF), TPO, and the like. Among these, TPO, VEGF, SCF, and the like are preferable.

The amount of cytokine added to the culture solution is appropriately determined depending on the type of cytokine and the properties of the cells. When using cells isolated from mouse bone marrow tissues, the addition amount is about 1 to 50 ng/ml for TPO, about 1 to 50 μg/ml for VEGF, and about 1 to 100 ng/ml for SCF, but not limited thereto.

After completion of the culture period, produced platelets are collected from the culture solution by centrifugation concentration or the like. When taking out the composite membrane from the culture solution, the cells (including platelets) may be washed down from the surface of the porous thin membrane and the inside of the porous support membrane by a pipetting operation. When using a closed-type culture system as shown in FIG. 5, the same culture solution, PBS solution, and the like as used in the culture system may be added to the culture vessel to wash down the suspended cell solution including produced platelets by the liquid flow, and the produced platelets may be collected by centrifugation concentration from the suspended cell solution.

The present invention provides platelets and/or megakaryocytes by culturing and inducing the platelet precursor cells. Platelets refer here to small cells which are produced from megakaryocytes, and have a size of 2 to 4 μm, and Platelets have a hemostatic function. Platelets include a platelet-derived growth factor (PDGF), a transforming growth factor (TGF), serotonin, and the like, and have an angiogenesis-promoting activity, a smooth muscle-contracting activity, and the like. Platelets express integrin (GPIIb/IIIa), and are fractionated in a specific region by flow cytometry. Therefore, the differentiated cells can be confirmed to be platelets. Megakaryocytes are cells that are produced by differentiation of hematopoietic stem cells into precursor cells (which are referred to as megakaryocyte colony forming cells) in the bone marrow similar to leucocytes and red cells, and further differentiation from undifferentiated cells referred to as megakaryoblasts. In this case, cell division occurs from several to ten and several times. Megakaryocytes have a diameter of 40 to 100 μm. In the bone marrow, megakaryocytes are normally observed right under the vascular endothelial cells in the sinus venosus. A protuberance appears from several places of the cytoplasm, and a long and thin cell process is formed from the cytoplasm. The cell process extends to form archetype of platelet that is connected as beads. Further, the archetype of platelet like beads is divided to form free platelets. 4000 to 6000 platelets are formed from one megakaryocyte.

The measuring methods used in the present invention are as follows.

(1) Average pore diameter D, pore diameter standard deviation σd, porosity, and ratio of number of through pores of porous thin membrane which constitutes the composite membrane The average pore diameter D, the pore diameter standard deviation σd, and the porosity, and the ratio of the number of through pores of the porous thin membrane are calculated by photographing the porous thin membrane using an optical microscope or a scanning electron microscope in the direction perpendicular to the surface of the porous thin membrane, and analyzing the pores of the porous thin membrane (sum of through pores and non-through pores) which are observed in the resulting planar image (photograph).

Specifically, the composite membrane is punched into a square sample (6.7×6.7 cm) around the center of the composite membrane. The center of the sample is referred to as point A, the four corners of the sample are referred to as B', C', D', and E', and the midpoints between the point A and the points B', C', D', and E' are respectively referred to as B, C, D, and E. The sample is photographed using a scanning electron microscope ("S-3000N" manufactured by Hitachi Ltd.) around the points A to E in the direction perpendicular to the sample surface to which the porous thin membrane is bonded (magnification: 1000 to 3000).

The resulting five photographs are captured respectively using image analysis software (Image-Pro Plus (Version 4.0 for Windows (registered trademark), manufactured by Media Cybernetics). An image area including about 200 pores is randomly selected in each photograph respectively. The contrast is adjusted so that the pore areas in the entire photograph can be automatically identified, and the average pore diameter is automatically calculated. Since the shape of most of the pores is not a perfect circle, the diameter of each pore is calculated from the average value of the major axis and the minor axis, and averaged. The resulting five average pore diameters are further averaged to obtain the average pore diameter D. When the pore area cannot be automatically identified by only the automatic contrast adjustment using the image analysis software, a manual operation is required, such as previously blacking out the pore portion in the photograph captured in the image analysis software.

The pore diameter standard deviation σd is a value obtained by further averaging the standard deviations of the pore diameters in the five image areas used to determine the above "average pore diameter D". The "porosity" is a value obtained by averaging the five porosities determined for the above image areas. These values can also be calculated by the above image analysis.

The ratio of the number of through pores is calculated by counting the total number N1 of pores (sum of through pores and non-through pores) included in each photograph in the five image areas used to calculate the above D, σd and porosity and the number N2 of pores that are formed through the porous thin membrane, calculating "N2/N1×100(%)" respectively, and calculating the average value of these five values.

(2) Measurement of average thickness T and thickness standard deviation σt of porous thin membrane of composite membrane, and observation of cross-sectional pore structure observation The composite membrane that has been immersed in ethanol, frozen with liquid nitrogen, and cut, so as to be able to observe the cross section of the membrane, is gently immobilized on a disk-like sample stage for a scanning electron microscope at a nonwoven fabric side using a double-faced adhesive tape or the like, and platinum is vapor deposited on the membrane (deposited film thickness is set to 12 nm). The membrane is observed using a scanning electron microscope ("S-3000N" manufactured by Hitachi Ltd.) in the direction beside the membrane (direction parallel with the membrane plane), and the average thickness T and the thickness standard deviation σt of the porous thin membrane of the composite membrane are measured.

Specifically, the cross section around each of the five points A to E selected when calculating the average pore diameter D in above (1) is observed using the scanning microscope, and the thickness of the porous thin membrane is calculated at intervals of 50 μm using the scale of the image. The thickness is measured at about 10 points per each of the five points, and the each average thickness is calculated. The resulting average thicknesses are averaged to obtain the "average thickness T". The thickness standard deviation σt is calculated using the resulting data.

(3) Measurement of average flow pore size of nonwoven fabric

The average flow pore size is determined by the half dry method in conformity to ASTM E1294-89 using a perm porometer (manufactured by PMI (Porous Materials, Inc.)). As an immersion liquid "SILWICK" (also manufactured by PMI, surface tension: 19.1 dyn/cm) was used.

(4) Measurement of average fiber diameter of nonwoven fabric

The nonwoven fabric of the composite membrane or the nonwoven fabric used to produce the composite membrane is observed using a digital microscope ("VT-8000" manufactured by Keyence Corporation). The diameters of the fine fibers and the ultrafine fibers are measured at 30 points, and the average value is calculated to obtain the average fiber diameter.

EXAMPLES

The present invention is further described in detail below by way of examples and comparative examples. Note that the present invention is not limited to the following examples.

Example 1

Culture of Hematopoietic Stem Cells Using Composite Membrane

1) Nonwoven Fabric

A three-layer web (spunbond long fiber web/melt-blown short fiber web/spunbond long fiber web) produced in the same manner as described in Examples 1 to 4 of WO2004/094136A1 was thermally compression bonded through a flat roll to obtain a polyethylene terephthalate three-layer nonwoven fabric. As a result of observation using an optical microscope and a scanning electron microscope, the nonwoven fabric was observed to have a structure in which long fibers (fine fibers) having an average fiber diameter of 15 μm and short fibers (ultrafine fibers) having an average fiber diameter of 1.6 μm were entangled and mixed.

The nonwoven fabric had an average flow pore size of 10.4 μm, a total weight per unit area (weight of fibers per $m^2$ of nonwoven fabric) of 20 $g/m^2$, and a thickness of 0.034 mm. The ratio of the weight of the fine fibers to the total weight of the fine fibers and the ultrafine fibers was 17 wt %.

2) Hydrophilization (Coating) of Nonwoven Fabric

A 0.2 wt % ethanol solution of a random copolymer of 2-hydroxyethyl methacrylate (HEMA) and 2-(N,N-dimethylamino)ethyl methacrylate (DMAMA) (HEMA/DMAMA=97/3 (molar ratio)) was prepared as a coating solution. The nonwoven fabric was continuously immersed in the coating solution for 5 seconds, and excess coating solution was removed by nipping the nonwoven fabric between and passing through a nip roll. The nonwoven fabric was then dried to obtain a coated nonwoven fabric. The copolymer was synthesized in accordance with the method described in Example 1-1-1 of WO2005/014149A1.

3) Production of Composite Membrane

A polysulfone (PSU: "UDEL P-3500" manufactured by Teijin Amoco Engineering Plastics Ltd) and a polyacrylamide amphiphilic polymer (see formula (I) below) as a solute were dissolved in chloroform as a solvent to prepare a 1.0 g/l hydrophobic organic solvent solution. The weight ratio of the PSU to the polyacrylamide amphiphilic polymer was 9/1. The polyacrylamide amphiphilic polymer shown by the chemical formula (I) was synthesized in accordance with the method described in Example 1-2 of WO2005/014149A1. The amphiphilic polymer was a random copolymer in which the molar ratio of the unit m to the unit n was m/n=4/1.

The coated nonwoven fabric prepared in 2) was cut into a square (16×16 cm), immersed in purified water in a beaker, and allowed to sufficiently hold water while deaerating for 5 minutes using an ultrasonic cleaner. The nonwoven fabric sufficiently holding water (water-containing nonwoven fabric) was taken out from the beaker, and placed on a glass plate. A metal frame punched into a square 10 cm on a side with a thickness of 1 mm was placed on the nonwoven fabric so that the water-containing nonwoven fabric was exposed from the entire punched out area of the metal frame. The glass plate, the water-containing nonwoven fabric, and the metal frame were secured in the overlapping state using a clip.

14 $cm^3$ of the prepared chloroform solution of PSU and the polyacrylamide amphiphilic polymer was gently poured into the punched out area of the metal frame where the water-containing nonwoven fabric was exposed therefrom, and chloroform was removed by spraying air with a relative humidity of 60% at a rate of 6 l/min onto the surface of the solution in a constant temperature and humidity room having a temperature of 25° C. and a relative humidity of 40% to form a porous thin membrane containing the PSU as the main component on the water-containing nonwoven fabric. After removing the metal frame, the nonwoven fabric was air-dried at room temperature to obtain a composite membrane.

The thickness of the composite membrane was 35 μm. The porous thin membrane had a porosity of 45%, an average pore diameter D of 3.8 μm, a ratio σd/D of 0.20, and the ratio of the through pores of 68%. The porous thin membrane had an average thickness T of 3.0 μm and a ratio σt/T of 0.20.

Figure 6:
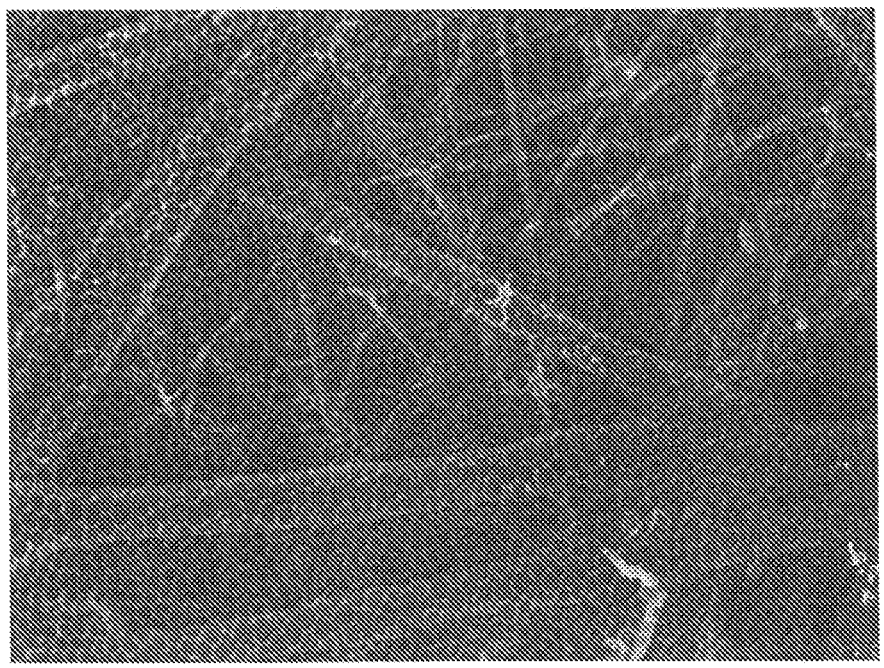
FIG. 6 shows a scanning electron micrograph of the surface of a composite membrane obtained in Example 1 on the side of a porous thin membrane.
Figure 7:
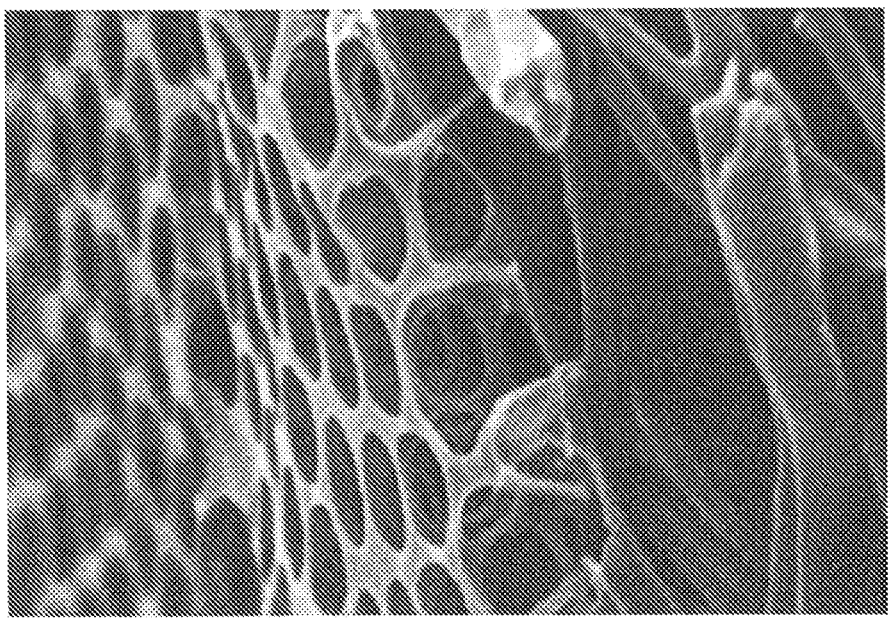
FIG. 7 shows a scanning electron micrograph of the cross section of a composite membrane (porous thin membrane area) obtained in Example 1.

FIG. 6 shows a scanning electron micrograph of the surface of the composite membrane observed from the side of the porous thin membrane. The thick fibers which can be seen at the bottom, upper left, and center of the micrograph are the long fibers of the nonwoven fabric having an average fiber diameter of 15 μm, and the numerous thin fibers observed among the thick fibers are ultrafine short fibers of the nonwoven fabric having an average fiber diameter of 1.6 μm. The numerous honeycomb-shaped pores are the pores of the porous thin membrane. The structure of the nonwoven fabric can be observed through the pores of the porous thin membrane. It was found that the porous thin membrane did not break. The fibers of the nonwoven fabric are introduced into (bonded to) the porous thin membrane, as the result, it can be also observed the state that the pores are closed. FIG. 7 shows a scanning electron micrograph of the cross section of the composite membrane around the porous thin membrane. The pores of the porous thin membrane have a structure of through pores which are expand spherically inside the membrane. Adjacent pores may be observed to communicate each other in the direction parallel to the surface of the membrane.

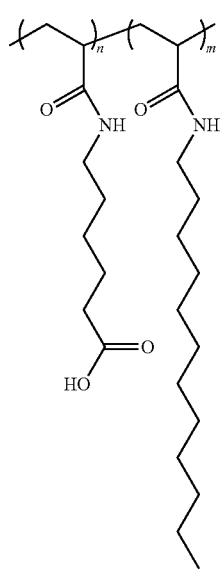

(I)

m/n = 4/1

4) Culture of Mouse Hematopoietic Stem Cells

The produced composite membrane was cut into a disc shape having a diameter of 25 mm, and the nonwoven fabric surface of the composite membrane was bonded to one end face of a glass ring (inner diameter: 22 mm, outer diameter: 25 mm, height: 10 mm) to obtain a cup-shaped vessel. A PSU chloroform solution (polymer concentration: 17%) was used as an adhesive.

The cup-shaped vessel was sterilized at 121° C. for 20 minutes using an autoclave, and placed on a water-absorbing sheet (cellulose nonwoven fabric, sterilized using autoclave) so that the composite membrane was positioned at the bottom. A suspension (including 500 cells) of hematopoietic stem cells isolated from bone marrow cells of a mouse (Green Mouse; GFP fluorescence protein transgenic mouse) was added dropwise to the composite membrane in the cup-shaped vessel. Most of the liquid passed through the composite membrane and was absorbed by the water-absorbing sheet. A cup-shaped vessel containing the composite membrane into which the hematopoietic stem cells were introduced was thus obtained.

The suspension of the mouse hematopoietic stem cells was prepared as follows. A thighbone was taken out from ten mice (eight week-old), and a bone marrow solution was prepared by a normal method. The cells were stained with an Lin antibody (prepared by mixing CD4, CD8, Gr-1, Mac-1, B220, and TER119 antibodies, a combination that can recognize matured blood cells, manufactured by Pharmingen) and a c-kit antibody (manufactured by Pharmingen) or an Sca-1 antibody (manufactured by Pharmingen). The Lin-negative, c-kit-positive, and Sca-1-positive hematopoietic stem cells were fractionated and collected by flow cytometry using an automatic fluorescence cell collector (JSAN; manufactured by eBiosystems), and the collected hematopoietic stem cells were added to a culture solution prepared by adding 10% bovine serum, SCF (50 ng/ml), TPO (10 ng/ml), and VEGF (10 ng/ml) (all of which manufactured by GIBCO) to an RPMI1640 base medium (manufactured by Sigma) so as to have a concentration of 500 cells/ml.

Four wells No. 1 to 4 were arbitrarily selected from a 6-well culture plate. 3 ml of the culture solution prepared by adding 10% bovine serum, SCF (50 ng/ml), TPO (10 ng/ml), and VEGF (10 ng/ml) to an RPMI1640 base medium was added to the well No. 1.

The cup-shaped vessel containing the composite membrane into which the hematopoietic stem cells were introduced was placed in the well No. 1, and the cells were cultured at 5% $CO_2$ and 37° C. The wells No. 2 to 4 were used in following Example 2 and Comparative examples 1 and 2.

Figure 8:
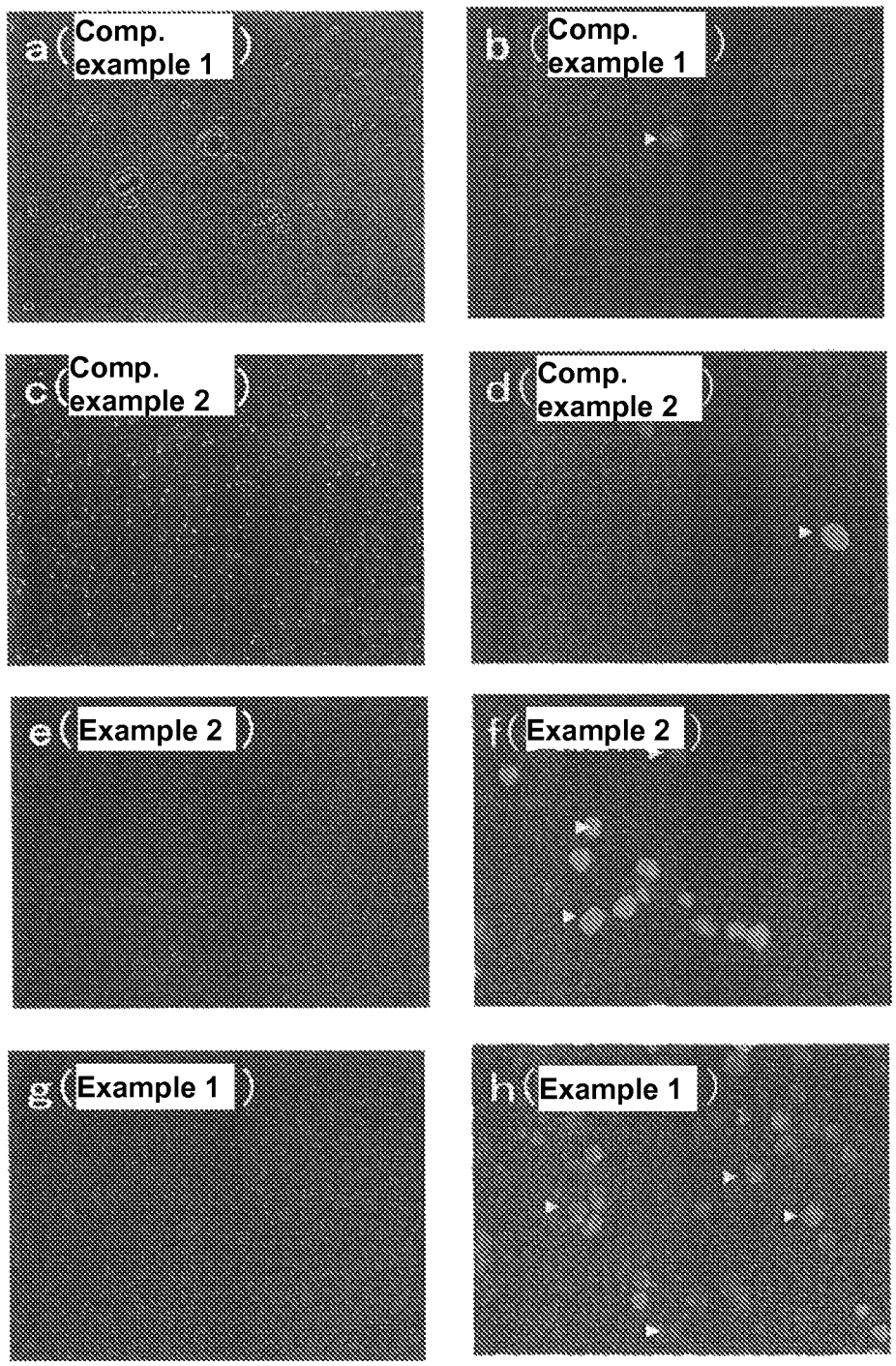
FIG. 8 shows an inverted photomicrograph of cells cultured in Examples 1 and 2 and Comparative examples 1 and 2. Photographs a and b: Comparative example 1. Hematopoietic stem cells were cultured in a culture plate using a culture solution including SCF (50 ng/ml), TPO (10 ng/ml), and VEGF (10 ng/ml) for 10 days. (a) Bright-field image. (b) Fluorescent image. A small amount of blood cells and a small amount of megakaryocytes are observed (b, arrowhead). Photographs c and d: Comparative example 2. Hematopoietic stem cells were cultured in a culture solution similar to Comparative example 1 for 10 days in a cup-shaped vessel containing a commercially available membrane having pores with a size of 0.4 µm. (c) Bright-field image. (d) Fluorescent image. A small amount of blood cells and a small amount of megakaryocytes are observed (d, arrowhead). Photographs e and f: Example 2. Hematopoietic stem cells were cultured in a culture solution similar to Comparative example 1 for 10 days in a cup-shaped vessel containing a nonwoven fabric. (e) Bright-field image. (f) Fluorescent image. A large amount of blood cells and a large amount of megakaryocytes are observed (f, arrowhead). Photographs g and h: Example 1. Hematopoietic stem cells were cultured in a culture solution similar to Comparative example 1 for 10 days in a cup-shaped vessel containing a composite membrane. (g) Bright-field image. (h) Fluorescent image. A large amount of blood cells and a large amount of megakaryocytes are observed (h, arrowhead).
Figure 9:
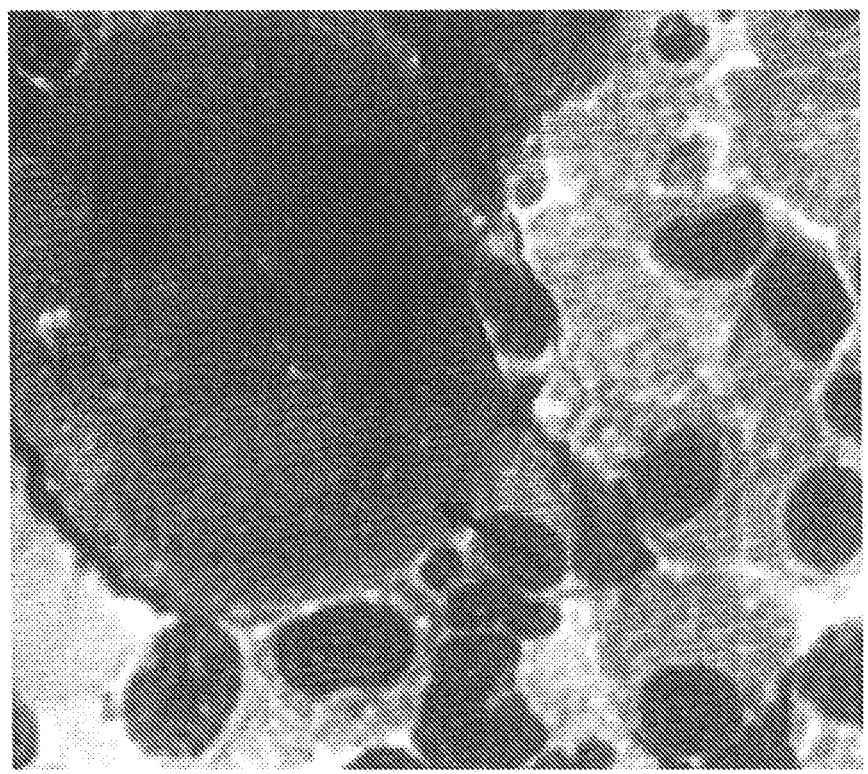
FIG. 9 shows a micrograph of blood cells subjected to May-Giemsa staining. Blood cells proliferated in the cup-shaped vessel of Example 1 were collected to prepare a cytospin preparation, and the blood cells were stained by the May-Giemsa method. Megakaryocytes having a diameter of 20 to 40 µm were observed (arrow).

5) Observation and Quantitative Determination of Produced Cells and Megakaryocytes After 10 days of the culture, the cells cultured in the well No. 1 were observed and photographed from bottom portion using an inverted fluorescence microscope (manufactured by Olympus Corporation) (see g (dark field image) and h (fluorescent image) in FIG. 8). As the result, number of large blood cells having a diameter of 20 to 40 μm were found to observe on the composite membrane. It was confirmed by the May-Giemsa staining method (arrow in FIG. 9) that the large blood cells having a diameter of 20 to 40 μm were megakaryocytes through the observation of the culture.

Figure 14:
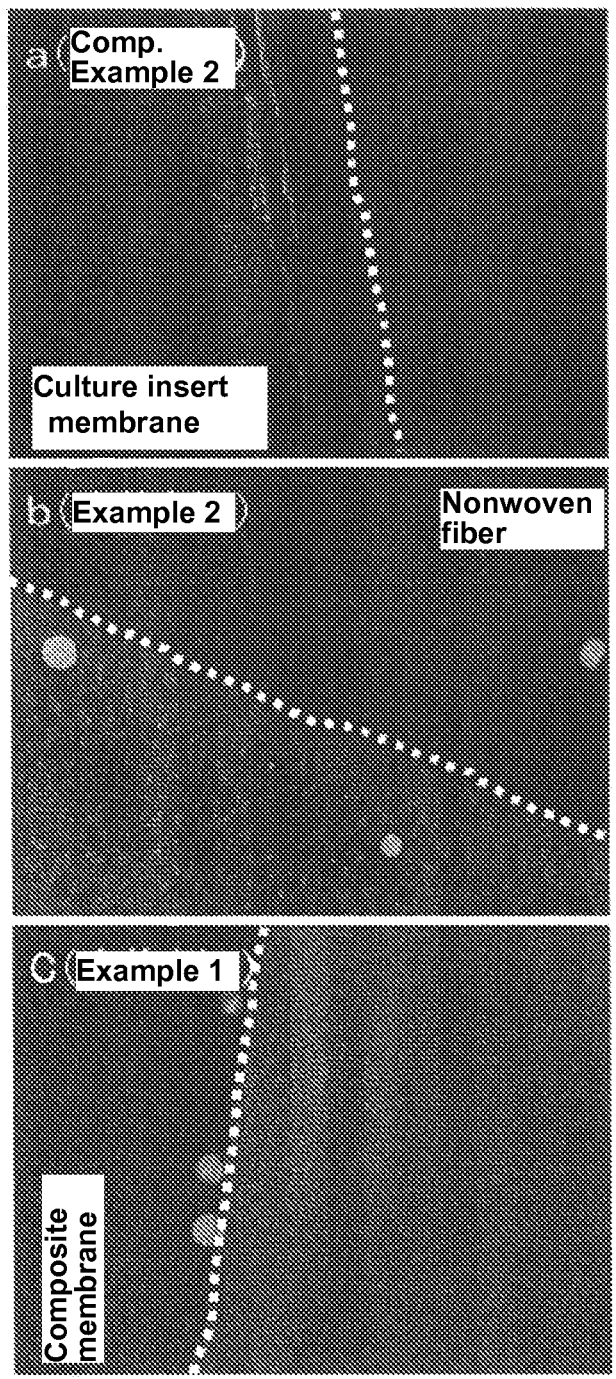
FIG. 14 shows an inverted fluorescence photomicrograph observed the membrane peripheral area from the lower part in Examples 1 and 2 and Comparative examples 1 and 2 after 10 days of culture. (a) Comparative example 2, (b) Example 2, (c) Example 1. Outflow of blood cells is not observed outside the cap in (a) and (c), but is observed in (b). The broken line indicates the border of the cup-shaped vessel.

Similarly after 10 days of the culture, the composite membrane area, the membrane peripheral area (around the bonding area with the glass ring), and the area in which the composite membrane was not present were also observed from bottom portion using the inverted fluorescence microscope. As shown in photograph c of FIG. 14, outflow of the cells was not observed in the area (the right side of the broken line; the broken line indicates the periphery of the effective porous thin membrane) of the culture solution in which the composite membrane was not present. It was thus confirmed that the porous thin membrane had a function of blocking outflow of the cells.

Figure 10:
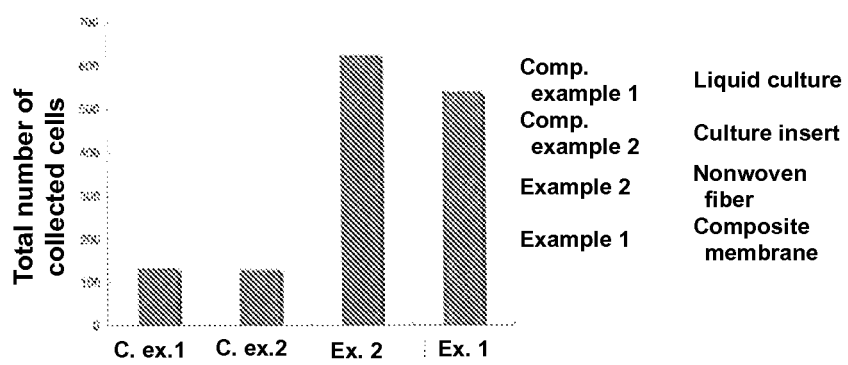
FIG. 10 is a table and a bar chart showing the total number of collected cells and the number of megakaryocytes obtained in Examples 1 and 2 and Comparative examples 1 and 2. A: A table showing the total number of collected cells and the number of megakaryocytes after 10 days of culture. B: A graph showing the total number of collected cells shown in the table. C: A graph showing the number of megakaryocytes shown in the table.
Figure 10:
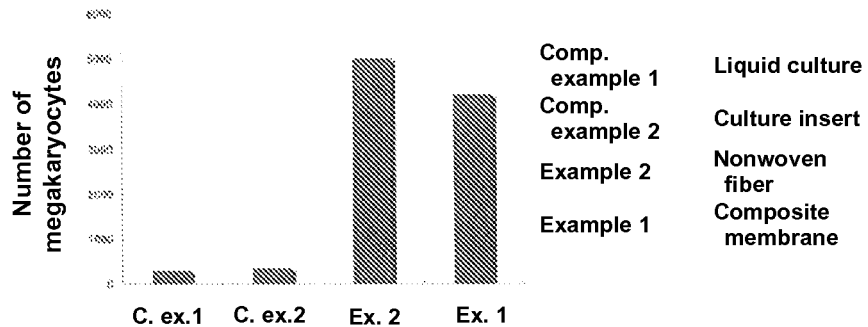

The culture solution inside and outside the cup-shaped vessel containing the composite membrane was collected, and the number of blood cells and the number of megakaryocyte were measured using a cytometer. The total number of collected cells was $5.40 \times 10^5$, and the number of megakaryocytes was 4200. FIG. 10 (A: table, B and C: bar chart) shows the total number of collected cells and the number of megakaryocytes together with the results for Example 2 and Comparative examples 1 and 2.

6) Quantitative Determination of Produced Platelets by Flow Cytometry

The cells obtained by 10 days of culture described in 5) were analyzed by flow cytometry using a Calibur (manufactured by Becton Dickinson). The ratio of platelet fraction cells was 1.13% of the total number of cells (d in FIG. 11). The number of platelets contained in the culture solution was found to be 6102 by calculating from the total number of collected cells based on the measured results. FIG. 12 (A: table, B: bar chart) shows the total number of platelets in comparison with the results for Example 2 and Comparative examples 1 and 2.

Example 2

Culture of Hematopoietic Stem Cells Using Only Nonwoven Fabric

The nonwoven fabric used in 1) of Example 1 was cut into a disc shape with diameter of 25 mm, and bonded to one end face of a glass ring (inner diameter: 22 mm, outer diameter: 25 mm, height: 10 mm) to obtain a cup-shaped vessel. The cup-shaped vessel was sterilized at 121° C. for 20 minutes using an autoclave. A PSU chloroform solution (polymer concentration: 17%) was used as an adhesive.

The cup-shaped vessel containing the nonwoven fabric was immersed in the well No. 4 (including the same culture solution as that in the well Nos. 1 to 3) of the 6-well culture plate provided in 4) of Example 1 so that the nonwoven fabric was positioned at the bottom, and 500 Green Mouse derived hematopoietic stem cells collected in the same manner as in Example 1 were cultured at 5% $CO_2$ and 37° C. Since the nonwoven fabric allowed the hematopoietic stem cells to easily pass through in this case, 2 ml of the culture solution was added to the well, and then the cup-shaped vessel was immersed and allowed to stand in the culture solution. 1 ml of the culture solution including 500 hematopoietic stem cells was then added dropwise to the vessel.

After 10 days of the culture, the cells cultured in the well No. 4 were observed from bottom portion using the inverted fluorescence microscope. A number of cells were observed inside the nonwoven fabric together with a number of megakaryocytes (e (dark field image) and f (fluorescent image) in FIG. 8). The culture solution was collected in the same manner as in 5) of Example 1, and the total number of cells and the number of megakaryocytes were calculated. The total number of collected cells was $6.25 \times 10^5$, and the number of megakaryocytes was 5000. FIG. 10 (A: table, B and C: bar chart) shows the total number of collected cells and the number of megakaryocytes together with the results for Example 1 and Comparative examples 1 and 2.

Similarly after 10 days of the culture, the nonwoven fabric area, the nonwoven fabric peripheral area (around the bonding area), and the area in which the nonwoven fabric was not present were also observed from bottom portion using the inverted fluorescence microscope. As shown in photograph b of FIG. 14, outflow of the cells was observed in the area (the lower side of the broken line; the broken line indicates the periphery of the effective nonwoven fabric) of the culture solution in which the nonwoven fabric was not present, differing from the case of using the composite membrane or a cell culture insert membrane. Specifically, since the nonwoven fabric does not have a function of blocking outflow of the cells, the cells cannot be cultured in a specific area (e.g., inside the nonwoven fabric) in the culture solution.

Figure 11:
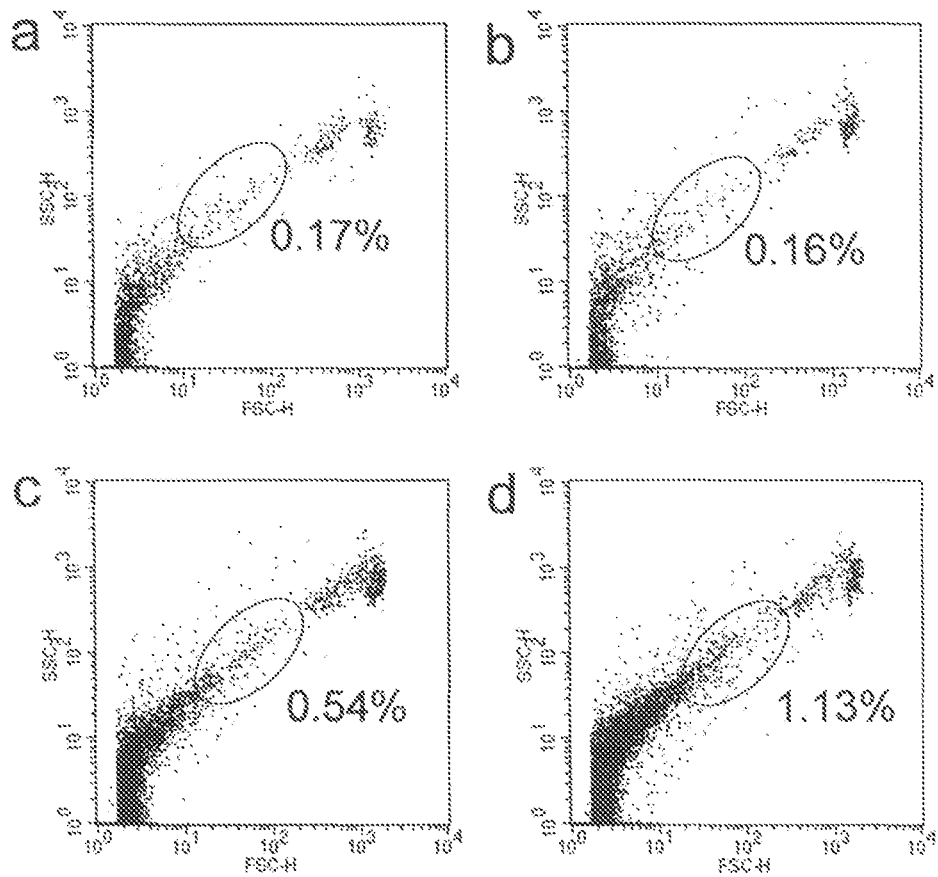
FIG. 11 shows a platelet fractionation analytical diagram determined by flow cytometry in Examples 1 and 2 and Comparative examples 1 and 2. An area enclosed by an oval indicates a platelet fraction. The value (%) indicates the ratio of the number of cells in the platelet fraction to the total number of cells. (a) Comparative example 1, (b) Comparative example 2, (c) Example 2, and (d) Example 1.
Figure 12:
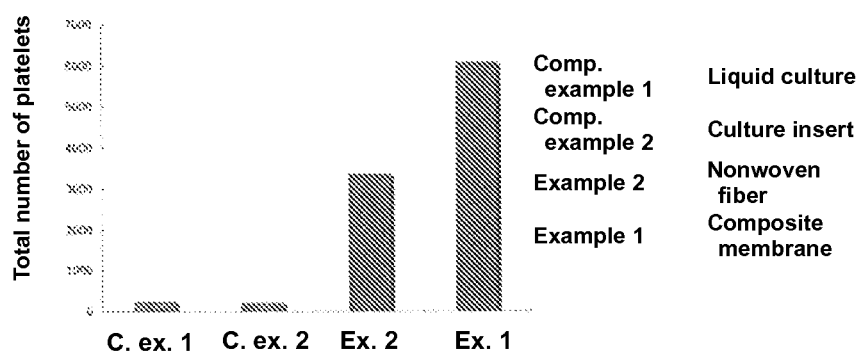
FIG. 12 is a table and a bar graph showing the total number of platelets obtained in Examples 1 and 2 and Comparative examples 1 and 2. A: A table showing the number of platelets. B: A bar graph showing the number of platelets shown in the table.

Platelet fraction was measured in the same manner as in 6) of Example 1 using the culture solution obtained by 10 days of culture, and the ratio of platelets was found to be 0.54% of the total number of cells (c in FIG. 11). It was confirmed that the number of platelets contained in the culture solution was calculated to be 3375 from the total number of cells.

FIG. 12 (A: table, B: bar chart) shows the total number of platelets together with the results for Example 1 and Comparative examples 1 and 2.

Example 3

Promotion of Platelet Release by Applying Shear Stress

Hematopoietic stem cells were cultured in a cup-shaped incubator for 10 days in the same manner as in Example 1-4). When megakaryocytes were being produced, the incubator was placed in a plastic culture dish with a diameter of 10 cm (containing 10 ml of a culture solution prepared by adding 10% bovine serum, SCF (50 ng/ml), TPO (10 ng/ml), and VEGF (10 ng/ml) (all manufactured by GIBCO) to an RPMI1640 base medium (manufactured by Sigma)). At the time, two capillary-blood tubes were apposed at the bottom of the culture dish, and the cup-shaped incubator was placed thereon so that a clearance gap of about 2 mm was formed between the culture dish and the cup-shaped incubator.

Figure 15:
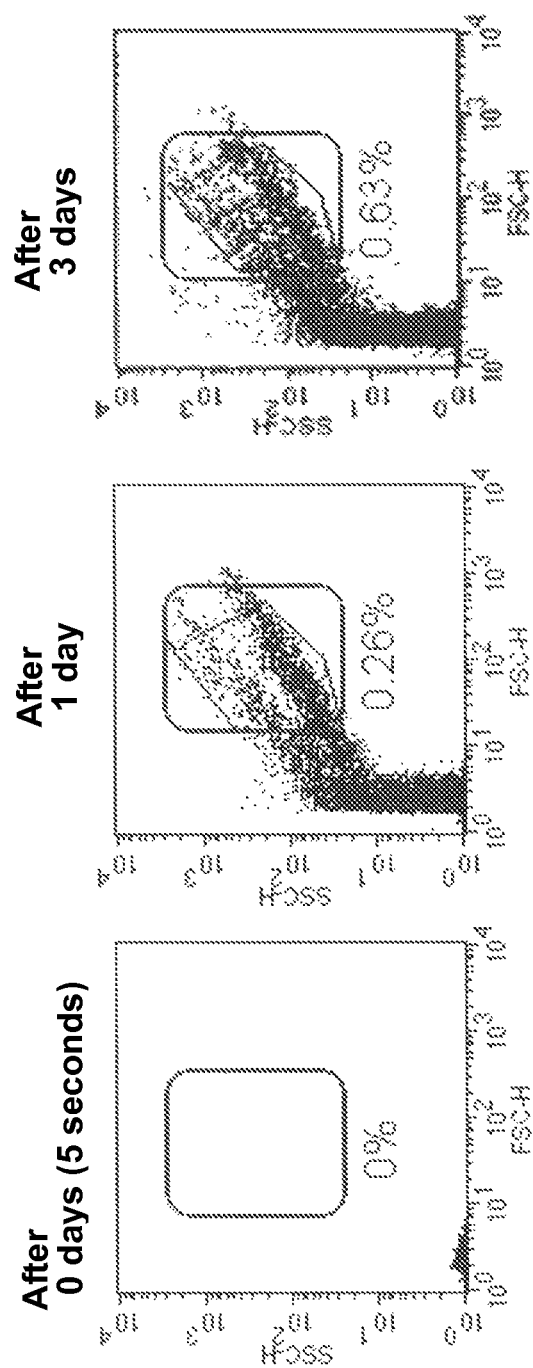
FIG. 15 shows the flow cytometric analysis results for platelets in the culture solution outside the cup-shaped incubator after applying a shear stress to the composite membrane after culturing hematopoietic stem cells for 10 days in the same manner as in Example 1. A red frame indicates a platelet fraction, and the value (%) indicates the ratio of platelets with respect to the whole cells.

A stirrer bar having a length of 2 cm was provided at a position about 3 cm away from the cup-shaped incubator placed in the culture dish. A liquid flow was caused to occur in the culture solution by a rotational speed of 200 rpm so that a fluid shear stress was applied to the porous thin membrane (integrated with the composite membrane) at the bottom of the cup-shaped incubator. The culture solution outside the cup-shaped incubator was collected 0 days (5 sec), 1 day, and 3 days after applying a shear stress, and platelets released from the porous membrane of the composite membrane were analyzed by flow cytometry (FIG. 15). No platelets were present in the culture solution outside the cup-shaped incubator immediately after (5 sec) applying a shear stress. However, release of platelets was promoted after 1 day and 3 days after applying a shear stress.

Comparative Example 1

Culture of Hematopoietic Stem Cells Using Only Liquid Component 3 ml of the same culture solution as added to the well No. 1 was added to the well No. 2 of the 6-well culture plate provided in 4) of Example 1, and 500 Green Mouse hematopoietic stem cells collected in the same manner as in Example 1 were seeded and cultured at 5% $CO_2$ and 37° C.

After 10 days of the culture, the cells in the well were observed from bottom portion using the inverted fluorescence microscope. A small number of cells were observed on the culture plate, and megakaryocytes were also included among them (a (dark field image) and b (fluorescent image) in FIG. 8). The culture solution was collected in the same manner as in 5) of Example 1, and the total number of cells and the number of megakaryocytes were calculated. The total number of collected cells was $1.33 \times 10^5$, and the number of megakaryocytes was 310 so little. FIG. 10 (A: table, B and C: bar chart) shows the total number of collected cells and the number of megakaryocytes together with the results for Examples 1 and 2 and Comparative example 2.

Platelet fraction was measured in the same manner as in 6) of Example 1 using the culture solution obtained by 10 days of culture, and the ratio of the platelets was found to be 0.17% of the total number of cells (a in FIG. 11). It was confirmed that the number of platelets contained in the culture solution was calculated to be 225 from the total number of cells. FIG. 12 (A: table, B: bar chart) shows the total number of platelets together with the results for Examples 1 and 2 and Comparative example 2.

Comparative Example 2

Culture of Hematopoietic Stem Cells Using Cell Culture Insert Membrane

Green Mouse hematopoietic stem cells were cultured at 5% $CO_2$ and 37° C. in the same manner as in Example 1, except for using a cup-shaped vessel containing a commercially available cell culture insert membrane with pore size of 0.4 μm (manufactured by FALCON; for 6 wells) instead of the cup-shaped vessel containing the composite membrane. The cell culture insert membrane was a single-layer membrane made of polyethylene terephthalate, and having linear tubular pores. The cell culture insert membrane had a thickness of about 15 μm and a porosity of about 5%.

Specifically, 3 ml of the same culture solution as added to the wells Nos. 1 and 2 was added to the well No. 3 of the 6-well culture plate provided in 4) of Example 1. The cup-shaped vessel containing the cell culture insert membrane on which hematopoietic stem cells were placed on the membrane surface inside the cup was immersed and allowed to stand in the culture solution.

After 10 days of the culture, the cells cultured in the well No. 3 were observed from bottom portion of the well using the inverted fluorescence microscope. A small number of cells were observed on the culture dish, and megakaryocytes were also included among them (c (dark field image) and d (fluorescent image) in FIG. 8). The culture solution was collected in the same manner as in 5) of Example 1, and the total number of cells and the number of megakaryocytes were calculated. The total number of collected cells was $1.30 \times 10^5$, and the number of megakaryocytes was 355 so small. FIG. 10 (A: table, B and C: bar chart) shows the total number of collected cells and the number of megakaryocytes in comparison with the results for Example 1 and Comparative examples 1 and 3.

Similarly after 10 days of culture the cell culture insert membrane area, the cell culture insert membrane peripheral area (around the bonding area), and the area in which the cell culture insert membrane was not present were also observed from bottom portion of the well using the inverted fluorescence microscope. As shown in photograph a of FIG. 14, outflow of the cells was not observed in the area (the right side of the broken line; the broken line indicates the border of the effective cell culture insert membrane) of the culture solution in which the membrane was not present.

Platelet fraction was measured in the same manner as in 6) of Example 1 using the culture solution obtained by 10 days of culture, and the ratio of the platelets was found to be 0.16% of the total number of cells (b in FIG. 11). It was confirmed that the number of platelets contained in the culture solution was calculated to be 208 from the total number of cells. FIG. 12 (A: table, B: bar chart) shows the total number of platelets together with the results for Examples 1 and 2 and Comparative example 1.

<Discussion>

The following effects of the present invention were confirmed from the above results for Examples 1 and 2 and Comparative examples 1 and 2.

(1) Induction from Hematopoietic Stem Cells to Megakaryocytes

When culturing an identical amount (number) of hematopoietic stem cells in a culture solution including identical components, the total number of collected cells produced by the culture system provided with the nonwoven fabric that provides a three-dimensional culture environment (Example 1 (composite membrane) and Example 2 (only nonwoven fabric)) was about five times in comparison with that of Comparative example 1 (only liquid component) and Comparative example 2 (cell culture insert membrane).

The number of megakaryocytes produced by the culture system provided with the nonwoven fabric (Examples 1 and 2) was about fifteen times in comparison with that of Comparative examples 1 and 2. These results suggest that the porous support membrane (particularly nonwoven fabric) used in the present invention has functions of promoting amplification of hematopoietic stem cells, and in addition thereto effectively promoting differentiation induction into megakaryocytes.

(2) Induction from Megakaryocytes to Platelets

Figure 13:
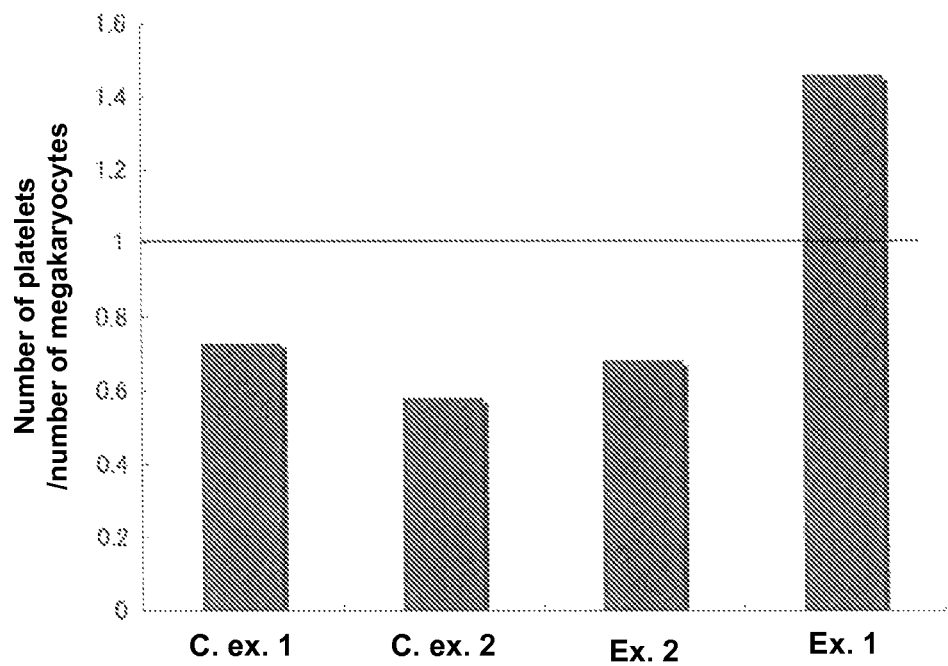
FIG. 13 is a bar chart showing the ratio of the number of platelets to the number of megakaryocytes (number of platelets/number of megakaryocytes) obtained in Examples 1 and 2 and Comparative examples 1 and 2.

The number of platelets produced in Example 1 (composite membrane) was about thirty times that of Comparative example 1 (only liquid component) and Comparative example 2 (cell culture insert membrane), and was about twice that of Example 2 (only nonwoven fabric). FIG. 13 shows the results that the efficiency of platelet production from megakaryocytes was calculated from the ratio of the number of platelets to the number of megakaryocytes (number of platelets/number of megakaryocytes).

Note that it is considered that one megakaryocyte may produce a plurality of platelets, and some megakaryocytes may produce no platelets. FIG. 13 shows just averaged values. The ratio of the number of platelets to the number of megakaryocytes produced in Example 1 was higher than 1 differing from Comparative examples 1 and 2. It was confirmed that platelet production can be most efficiently induced by Example 1. These results suggest that the porous thin membrane used in the present invention has a function of specifically inducing production of platelets from megakaryocytes.

(3) Production of Megakaryocytes from Hemopoietic Stem/Precursor Cells, and Production of Platelets from Megakaryocytes The composite membrane used in the present invention functions as a scaffold that may promote both production of megakaryocytes from hemopoietic stem/precursor cells, and production of platelets from megakaryocytes. Therefore, the induction method using the composite membrane according to the present invention is useful for in vitro production of platelets from platelet precursor cells. Since the porous thin membrane of the composite membrane plays a role in blocking outflow of the platelet precursor cells (particularly nucleated cells) from the porous support membrane side to opposite side, the induction method using the composite membrane according to the present invention has high practical value taking account of clinical applications of produced platelets.

INDUSTRIAL APPLICABILITY

In vitro platelet production using undifferentiated hematopoietic cells derived from the bone marrow or cord blood as a stem cell source is characterized in that a rejection response and a virus infection risk when transfusing the produced platelets are extremely low. However, since the number of undifferentiated hematopoietic cells which can be obtained from a living body is very small, it is considered to be inappropriate as the stem cell source. However, since the induction method according to the present invention implements a high megakaryocyte induction efficiency from hemopoietic stem/precursor cells and a high platelet production efficiency from megakaryocytes, a practical platelet transplant treatment from hemopoietic stem/precursor cells derived from the bone marrow or cord blood is expected to be implemented by utilizing the method according to the present invention either alone or in combination with known conventional technology.

Moreover, since the method according to the present invention can be applied to platelet production technology using adult stem cells or embryonic stem cells (ES cells) that have attracted attention as a stem cell source that may solve a deficiency in stem cells derived from the living body as described above, or induced pluripotent stem cells (IPS cells) that are expected to solve an ethical problem of ES cell and a problem a rejection response, the method according to the present invention has a very high technical contribution.

It is considered that a stable and safe blood transfusion treatment will be widespread in the near future by gradually replacing platelets repeatedly transplanted to patients suffering from thrombocytopenia or the like with platelets produced in vitro based on the above technology. It is expected that the current transfusion business that relies upon volunteer donors will be replaced by a so-called "blood factory" that safely mass-produces blood components such as platelets, red cells, and lymphocytes.

In recent years, attempts have been made to transplant megakaryocytes as a means to recover the platelet for a patient with decreased platelet (see haematologica 2004; 89(5): May 2004, for example). As described above, the composite membrane used in the present invention is effective for inducing megakaryocytes from hematopoietic stem cells. Therefore, the method according to the present invention is also useful as a megakaryocyte induction method when using undifferentiated cells such as hemopoietic stem/precursor cells, ES cells, iPS cells or the like as the platelet precursor cells. Therefore, it is expected that the method according to the present invention will be used for the research of in vivo and in vitro platelet induction technology, and may be developed into clinical applications using megakaryocytes.

EXPLANATION OF SYMBOLS

1 Cylindrical culture vessel
2 Multiple composite membranes disposed in parallel
3 Rectangular parallelepiped culture vessel
4 Multiple composite membranes disposed perpendicularly
5 Platelet precursor cell inlet
6 Culture solution inlet
7 Produced platelet suspension outlet
8 Composite membrane
9 Cup-shaped vessel
10 Culture solution vessel
11 Housing
12 Stirrer

The invention claimed is:

1. A method for making and isolating platelets comprising: culturing platelet precursor cells in a vessel which contains therein a composite membrane, wherein the composite membrane is a porous support membrane with at least one porous thin membrane provided on at least one side of the porous support membrane, such that the platelet precursor cells are confined within the composite membrane; the porous thin membrane having a porosity of 5 to 80%, an average pore diameter D of 0.5 to 20 µm, and a ratio ($\sigma d/D$) of a pore diameter standard deviation $\sigma d$ (µm) to the average pore diameter D of 0 to 0.6, and the porous support membrane having an average flow pore size of 1 µm or more; inducing differentiation of the platelet precursor cells into platelets such that the platelets flow through the composite membrane but the platelet precursor cells are maintained within the composite membrane; and collecting the platelets.

2. The method according to claim 1, comprising applying a shear stress to the platelet precursor cells to promote differentiation of the platelet precursor cells into platelets.

3. The method according to claim 1, wherein the porous thin membrane has an average thickness T of 0.5 to 30 µm, and a ratio ($\sigma t/T$) of a thickness standard deviation $\sigma t$ (µm) to the average thickness T of 0 to 0.5.

4. The method according to claim 1, wherein the porosity of the porous thin membrane is 10 to 80%.

5. The method according to claim 1, wherein the porosity, the average pore diameter D and an average thickness T of the porous thin membrane are 15 to 80%, 0.5 to 10 µm and 0.5 to 15 µm, respectively.

6. The method according to claim 2, wherein the porous thin membrane has an average thickness T of 0.5 to 30 µm, and a ratio ($\sigma t/T$) of a thickness standard deviation $\sigma t$ (µm) to the average thickness T of 0 to 0.5.

7. The method according to claim 2, wherein the porosity of the porous thin membrane is 10 to 80%.

8. The method according to claim 3, wherein the porosity of the porous thin membrane is 10 to 80%.

9. The method according to claim 2, wherein the porosity, the average pore diameter D and an average thickness T of the porous thin membrane are 15 to 80%, 0.5 to 10 µm and 0.5 to 15 µm, respectively.

10. The method according to claim 3, wherein the porosity, the average pore diameter D and an average thickness T of the porous thin membrane are 15 to 80%, 0.5 to 10 µm and 0.5 to 15 µm, respectively.

11. The method according to claim 4, wherein the porosity, the average pore diameter D and an average thickness T of the porous thin membrane are 15 to 80%, 0.5 to 10 µm and 0.5 to 15 µm, respectively.

* * * * *